US011961595B2

(12) United States Patent
Madrid et al.

(10) Patent No.: US 11,961,595 B2
(45) Date of Patent: Apr. 16, 2024

(54) COMPUTATIONAL GENERATION OF CHEMICAL SYNTHESIS ROUTES AND METHODS

(71) Applicant: SRI INTERNATIONAL, Menlo Park, CA (US)

(72) Inventors: Peter Madrid, San Jose, CA (US); Nathan Collins, Menlo Park, CA (US); Mario Latendresse, Menlo Park, CA (US); Jeremiah Malerich, Menlo Park, CA (US); Markus Krummenacker, Menlo Park, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 0 days.

(21) Appl. No.: 16/965,222

(22) PCT Filed: Jan. 30, 2019

(86) PCT No.: PCT/US2019/015868
§ 371 (c)(1),
(2) Date: Jul. 27, 2020

(87) PCT Pub. No.: WO2019/156872
PCT Pub. Date: Aug. 15, 2019

(65) Prior Publication Data
US 2021/0065851 A1    Mar. 4, 2021

Related U.S. Application Data

(60) Provisional application No. 62/640,282, filed on Mar. 8, 2018, provisional application No. 62/624,047, filed on Jan. 30, 2018.

(51) Int. Cl.
| | |
|---|---|
| *G01N 31/00* | (2006.01) |
| *G16C 10/00* | (2019.01) |
| *G16C 20/10* | (2019.01) |
| *G16C 20/70* | (2019.01) |
| *G16C 20/80* | (2019.01) |

(52) U.S. Cl.
CPC .............. *G16C 20/70* (2019.02); *G16C 10/00* (2019.02); *G16C 20/10* (2019.02); *G16C 20/80* (2019.02)

(58) Field of Classification Search
None
See application file for complete search history.

(56) References Cited

U.S. PATENT DOCUMENTS

| | | | |
|---|---|---|---|
| 2003/0087334 A1 | 5/2003 | Bunin et al. | |
| 2003/0220716 A1 | 11/2003 | Mydlowec et al. | |
| 2008/0177478 A1* | 7/2008 | Hlavacek | G16C 20/30 |
| | | | 702/19 |
| 2009/0209759 A1 | 8/2009 | Warrington et al. | |
| 2017/0116369 A1 | 4/2017 | Chowdhury et al. | |

FOREIGN PATENT DOCUMENTS

WO    03044219 A1    5/2003

OTHER PUBLICATIONS

Liu, Bowen, et al. "Retrosynthetic reaction prediction using neural sequence-to-sequence models." ACS central science 3.10 (2017): 1103-1113.*
Coley, Connor W., et al. "Prediction of organic reaction outcomes using machine learning." ACS central science 3.5 (2017): 434-443.*
Segler, Marwin HS, and Mark P. Waller. "Neural-symbolic machine learning for retrosynthesis and reaction prediction." Chemistry—A European Journal 23.25 (2017): 5966-5971.*
International Search Report and Written Opinion issued by the International Searching Authority dated Jul. 19, 2019, for PCT/US2019/015868, filed on Jan. 30, 2019 (8 pages).
Cho, A. et al., "Prediction of novel synthetic pathways for the production of desired chemicals," BMC Systems Biology, 2010, p. 35, vol. 4, No. 1.
Coley, C.W. et al., "Prediction of Organic Reaction Outcomes Using Machine Learning," ACS Central Science, 2017, pp. 434-443, vol. 3, No. 5.
Delepine, B. et al., "RetroPath2.0: A restrosynthesis workflow for metabolic engineers," Metabolic Engineering, 2018, pp. 158-170, vol. 45.
Segler, H.S. et al., "Learning to Plan Chemical Syntheses," ARFXIV. org, Cornell University Library, 2017, pp. 1-19.
Warr, W., "A Short Review of Chemical Reaction Database Systems, Computer-Aided Synthesis Design, Reaction Prediction and Synthetic Feasibility," 2014, pp. 469-476, vol. 33, Nos. 6-7.
Extended European Search Report issued in related application No. EP19750518 dated Oct. 11, 2021.
Response to Office Action, and translation thereof, dated Feb. 22, 2023, from counterpart Japanese Application No. 2020-562104 filed Apr. 21, 2023, 15 pp.
"Daylight", Daylight Chemical Information Systems, Inc., Retrieved from: http://www.daylight.com., Accessed on: Feb. 9, 2023, 2 pp.
"SA Score implementation in RDKit", Retrieved from: https://raw.githubusercontent.com/rdkit/rdkit/master/Contrib/SA_Score/sascorer.py, Accessed on Mar. 23, 2022, 3 pp.
Bienfait et al., "JSME: a free molecule editor in JavaScript", Journal of Cheminformatics, vol. 5, No. 24, May 21, 2013, 6 pp.
Coley et al., "A robotic platform for flow synthesis of organic compounds informed by AI planning", Science, vol. 365, No. 6453, Aug. 9, 2019, p. 557.
Coley et al., "RDChiral: An RDKit Wrapper for Handling Stereochemistry in Retrosynthetic Template Extraction and Application", Journal of Chemical Information and Modeling, Jun. 13, 2019, pp. 2529-2537.
Collins et al., "Fully Automated Chemical Synthesis: Toward the Universal Synthesizer", Organic Process Research & Development, vol. 24, No. 10, Jun. 23, 2020, pp. 2064-2077.

(Continued)

*Primary Examiner* — Anna Skibinsky
(74) *Attorney, Agent, or Firm* — Shumaker & Sieffert, P.A.

(57) ABSTRACT

Retrosynthetic methods are described for determining one or more optimal synthetic routes to generate a target compound.

19 Claims, 22 Drawing Sheets

(56) References Cited

OTHER PUBLICATIONS

Corey et al., "Computer-Assisted Design of Complex Organic Syntheses", Science, vol. 166, No. 3902, Oct. 10, 1969, pp. 178-192.
Corey et al., "Computer-assisted synthetic analysis for complex molecules. Methods and procedures for machine generation of synthetic intermediates.", Journal of the American Chemical Society, vol. 94, No. 2, Jan. 1, 1972, pp. 440-459.
Corey et al., "Computer-assisted synthetic analysis. Facile man-machine communication of chemical structure by Interactive computer graphics", Journal of the American Chemical Society, vol. 94, No. 2, Jan. 1, 1972, pp. 421-430.
Dijkstra, "A Note on Two Problems in Connexion with Graphs", Numerische Mathematik, vol. 1, Dec. 1959, pp. 269-271.
Fortunato et al., "Data Augmentation and Pretraining for Template-Based Retrosynthetic Prediction in Computer-Aided Synthesis Planning", Journal of Chemical Information and Modeling, vol. 60, No. 7, Jun. 22, 2020, 24 pp.
Genheden et al., "AiZynthFinder: a fast, robust and flexible open-source software for retrosynthetic planning", Journal of Cheminformatics, vol. 12, No. 70, Nov. 17, 2020, 9 pp.
Heid et al., "In uence of Template Size, Canonicalization, and Exclusivity for Retrosynthesis and Reaction Prediction Applications", Journal of Chemical Information and Modeling, vol. 62, No. 1, Dec. 23, 2021, pp. 16-26.
Klucznik et al., "Efficient Syntheses of Diverse, Medicinally Relevant Targets Planned by Computer and Executed in the Laboratory", Chem, vol. 4, No. 3, Mar. 8, 2018, pp. 522-532.
Lin et al., "Improving the performance of models for one-step retrosynthesis through re-ranking", Journal of Cheminformatics, vol. 14, No. 15, Mar. 15, 2022, 13 pp.
Lowe, "Extraction of chemical structures and reactions from the literature", Ph.D. thesis, University of Cambridge, Jun. 2012, p. 210.
Pensak et al., "LHASA—Logic and Heuristics Applied to Synthetic Analysis", Computer-Assisted Organic Synthesis, Jun. 1, 1977, pp. 1-32.
Roughley et al., "The Medicinal Chemist's Toolbox: An Analysis of Reactions Used in the Pursuit of Drug Candidates", Journal of Medicinal Chemistry, vol. 54, No. 10, Apr. 19, 2011, pp. 3451-3479.
Salatin et al., "Computer-assisted mechanistic evaluation of organic reactions. 1. Overview", The Journal of Organic Chemistry, vol. 45, No. 11, May 23, 1980, pp. 2043-2051.
Satoh et al., "Sophia, a Knowledge Base-Guided Reaction Prediction System—Utilization of a Knowledge Base Derived from a Reaction Database", Journal of Chemical Information and Computer Sciences, vol. 35, No. 1, Jan. 1, 1995, pp. 34-44.
Schwaller et al., "Molecular Transformer: A Model for Uncertainty-Calibrated Chemical Reaction Prediction", ACS Central Science, Aug. 30, 2019, pp. 1572-1583.
Segler et al., "Planning chemical syntheses with deep neural networks and symbolic AI", Nature, vol. 555, Mar. 29, 2018, pp. 604-610.
Szeto et al., "Development of continuous flow processes in the synthesis of itraconazole", 260th ACS National Meeting & Exposition, 2020, 21 pp., (Applicant points out, in accordance with MPEP 609.04(a), that the year of publication, 2020, is sufficiently earlier than the effective U.S. filing date, so that the particular month of publication is not an issue.).
Vu et al., "Development of a continuous flow synthesis of bortezomib", 260th ACS National Meeting & Exposition, 2020, 15 pp., (Applicant points out, in accordance with MPEP 609.04(a), that the year of publication, 2020, is sufficiently earlier than the effective U.S. filing date, so that the particular month of publication is not an issue.).
Williams et al., "The Future of Retrosynthesis and Synthetic Planning: Algorithmic, Humanistic or the Interplay?", Australian Journal of Chemistry, vol. 74, May 12, 2021, pp. 291-326.
Ertl et al., "Estimation of synthetic accessibility score of drug-like molecules based on molecular complexity and fragment contributions", Journal of Cheminformatics 2009, Jun. 10, 2009, 11 pp.
Office Action, and translation thereof, from counterpart Japanese Application No. 2020-562104 dated Feb. 22, 2023, 4 pp.
Communication pursuant to Article 94(3) EPC from counterpart European Application No. 19750518.3 dated May 24, 2023, 5 pp.
Notice of Intent to Grant from counterpart Japanese Application No. 2020-562104 dated May 18, 2023, 4 pp.
Response to Office Action dated May 24, 2023, from counterpart Application No. 19750518.3 filed Sep. 19, 2023, 18 pp.
First Examination Report from counterpart Australian Application No. 2019217331 dated Oct. 25, 2023, 7 pp.

* cited by examiner

COMPUTATIONAL GENERATION OF CHEMICAL SYNTHESIS ROUTES AND METHODS

CROSS REFERENCE TO RELATED APPLICATION

This Application is a national stage filing under 35 U.S.C. § 371 of International Application No. PCT/US2019/015868, filed on Jan. 30, 2019, which claims priority to U.S. Provisional Application Nos. 62/640,282 filed Mar. 8, 2018, and 62/624,047, filed Jan. 30, 2018, herein incorporated by reference in their entireties.

STATEMENT REGARDING FEDERALLY SPONSORED RESEARCH

This invention was made with Government support under contract no. W911NF-16-C-0051 awarded by the Army Research Office. The Government has certain rights in this invention.

BACKGROUND

Retrosynthetic analysis is a problem solving technique for transforming the structure of a target compound to a sequence of progressively simpler structures along a synthetic route which ultimately leads to simple and/or commercially available starting materials (also referred to as "feedstock") for a chemical synthesis. Currently, chemists must rely on known chemical reactions in order to retrosynthetically construct a such a synthetic route. What is needed are techniques for enabling construction of a synthetic route that are not constrained to known chemical reactions.

SUMMARY

It is to be understood that both the following general description and the following detailed description are exemplary and explanatory only and are not restrictive. Methods and systems for determining synthetic routes are described.

A method is described for identifying one or more synthetic routes for producing a target compound comprising determining a plurality of known chemical reactions and/or a plurality of novel chemical reactions, determining, from the plurality of novel chemical reactions, a plurality of predicted chemical reactions, based on a trained classifier, generating a plurality of chemical reactions, based on the plurality of predicted chemical reactions and the plurality of known chemical reactions, determining at least one target compound, determining a plurality of chemical reaction routes associated with the at least one target compound, and determining one or more optimal chemical reaction routes from the plurality of chemical reaction routes identified for producing the target compound.

A method is described for identifying one or more synthetic routes for producing a target compound comprising training, based on a portion of a plurality of known chemical reactions, one or more machine learning classifiers, determining, based on the plurality of known chemical reactions, one or more known chemical reactions that result in a target compound, determining, based on chemical reaction transformations, one or more predicted chemical reactions that result in the target compound, wherein the one or more predicted chemical reactions are predicted as being successful by the one more machine learning classifiers, retrosynthetically determining a plurality of synthetic routes, wherein each synthetic route results in the target compound, wherein at least one synthetic route comprises at least one of the one or more known chemical reactions and at least one of the one or more predicted chemical reactions, and determining, based on a predetermined number of reactions and a cost function, an optimal synthetic route from the plurality of synthetic routes.

This summary is not intended to identify critical or essential features of the disclosure, but merely to summarize certain features and variations thereof. Other details and features will be described in the sections that follow.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
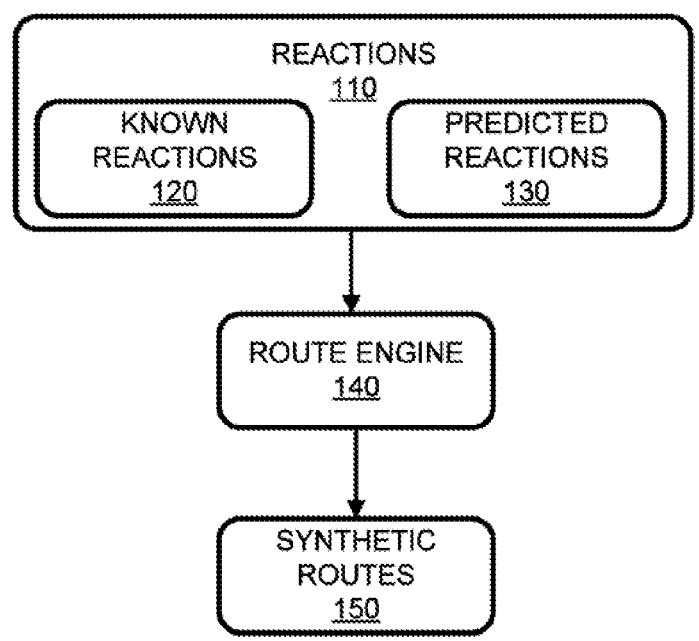
FIG. 1 shows an example process for determining synthetic routes.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another configuration includes from the one particular value and/or to the other particular value. When values are expressed as approximations, by use of the antecedent "about," it will be understood that the particular value forms another configuration. It will be further understood that the endpoints of each of the ranges are significant both in relation to the other endpoint, and independently of the other endpoint.

"Optional" or "optionally" means that the subsequently described event or circumstance may or may not occur, and that the description includes cases where said event or circumstance occurs and cases where it does not.

Throughout the description and claims of this specification, the word "comprise" and variations of the word, such as "comprising" and "comprises," means "including but not limited to," and is not intended to exclude other components, integers or steps. "Exemplary" means "an example of" and is not intended to convey an indication of a preferred or ideal configuration. "Such as" is not used in a restrictive sense, but for explanatory purposes.

It is understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (e.g., non-transitory) having processor-executable instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Throughout this application reference is made to block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a general purpose computer, special purpose computer, or other programmable data processing apparatus to produce a machine, such that the processor-executable instructions which execute on the computer or other programmable data processing apparatus create a device for implementing the functions specified in the flowchart block or blocks.

These processor-executable instructions may also be stored in a computer-readable memory that may direct a computer or other programmable data processing apparatus to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the processor-executable instructions that execute on the computer or other programmable apparatus provide steps for implementing the functions specified in the flowchart block or blocks.

Accordingly, blocks of the block diagrams and flowcharts support combinations of devices for performing the specified functions, combinations of steps for performing the specified functions and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

This detailed description may refer to a given entity performing some action. It should be understood that this language may in some cases mean that a system (e.g., a computer) owned and/or controlled by the given entity is actually performing the action.

In an aspect, methods and systems are described for generating synthetic strategies using retrosynthetic analysis. Strategy refers to a plan to synthesize a target compound. Retrosynthetic analysis is a problem solving technique for transforming the structure of a target compound to a sequence of progressively simpler structures along a pathway which ultimately leads to simple and/or commercially available starting materials (also referred to as "feedstock") for a chemical synthesis. The transformation of a compound to a synthetic precursor is accomplished by the application of a transform, the exact reverse of a synthetic reaction, to a target compound. Each structure derived antithetically from a target then itself becomes a target compound for a further analysis. Repetition of this process eventually produces a synthetic route (or simply, route) to the target compound, the synthetic route having chemical structures as nodes and edges as reactions.

A target compound can be selected for investigation and suitable routes for synthesis can be derived. Having chosen the target compound for synthesis, synthetic plans can be determined that would summarize some or all reasonable routes for the synthesis of the target compound. Retrosynthesis may be described as a logical disconnection at strategic bonds in such a way that the process would progressively lead to available starting material(s) through several synthetic plans. Each plan thus evolved, describes a route based on a retrosynthesis. Each disconnection leads to a simplified structure. The logic of such disconnections forms the basis for the retrosynthetic analysis of a given target compound. As described herein, a route can be generated using known chemical reactions and/or computationally generated chemical reactions. Thus, a synthetic tree can be constructed that can summarize some or all possible routes for the given target compound.

A route may be said to be efficient or optimal based on assessment of several parameters. For example, when the overall yield of the total process is the best amongst all routes investigated. This would depend not only on the number of steps involved in the synthesis, but also on the type of strategy followed. The strategy may involve linear syntheses involving only consequential steps or convergent syntheses involving fewer consequential steps. When each disconnection process leads to only one feasible intermediate and the process proceeds in this fashion all the way to one set of starting materials, the process is called a linear synthesis. When an intermediate could be disconnected in two or more ways leading to different intermediates, branching occurs in the plan. The processes could be continued all the way to starting materials. In such routes, different branches of the synthetic pathways converge towards an intermediate. Such schemes are called convergent syntheses.

As shown in FIG. 1, the methods and systems described rely on a plurality of reactions 110 for retrosynthesis. The reactions 110 can be comprised of both known reactions 120 and predicted reactions 130. The known reactions 120 may be derived from any source of known reactions, such as a reaction database. Reaction databases may comprise, for example, Reaxys, SciFinder, ChemInform or OrgSyn as well as proprietary reaction databases such as those from internal electronic laboratory notebooks. The predicted reactions 130 (computationally generated reactions) may be generated based on known reaction transformations, such as the MCT (Medicinal Chemist's Toolbox) which contains a set of reliable reactions commonly used by medicinal chemists (Roughley & Jordan, J. Med. Chem. 2011, 3451) incorporated herein by reference, lists of so-called "named reactions" or extracted computationally by clustering methods on databases of reactions to identify generalized reaction transformations (*J. Chem. Inf. Model.*, 2009, 49 (3), pp 593-602) incorporated herein by reference. A "reaction transformation" may be a generalization of the pattern of bonds being made and broken between the various atom types. The predicted reactions 130 may be classified as either successful or not successful through artificial intelligence techniques, such as machine learning and classification. For example, one or more of an artificial neural network, a support vector machine, boosted and bagged decision trees, a k-nearest neighbor technique, a Naïve Bayes technique, discriminant analysis, logistic regression, combinations thereof, and the like, may be used to classify the predicted reactions 130. Both the known reactions 120 and the predicted reaction 130 may be utilized by a route engine 140. The route engine 140 can receive a target compound as input and apply reaction transformations derived from the reactions 110 retrosynthetically to generate one or more synthetic routes 150.

Figure 2:
FIG. 2 shows an example process for training a machine learning classifier.

In an aspect, methods and systems are described for generating the predicted reactions 130 using artificial intelligence techniques. An example of generating the predicted reactions 130 using artificial intelligence techniques is shown in FIG. 2. The known reactions 120 may be used as training data to train a machine learning classifier. Machine learning includes any of several methods, devices, and/or other features which are optimized to perform a specific informational task (such as classification or regression) using examples of data of a given form, and are then capable of exercising this same task on unknown data of the same type and form. The machine (e.g., a computer) will learn, for example, by identifying patterns, categories, statistical relationships, etc., exhibited by training data. The result of the learning is then used to predict whether new data exhibits the same patterns, categories, statistical relationships. The machine learning classifier can be one or more of an artificial neural network, a support vector machine, boosted and bagged decision trees, a k-nearest neighbor technique, a Naïve Bayes technique, discriminant analysis, logistic regression, combinations thereof, and the like.

In order to train the machine learning classifier, the known reactions 120 can be processed to serve as training data by encoding the known reactions 120 at 210. Encoding the known reactions can comprise encoding all the atoms of the reactants according to a fixed set of properties. The properties can comprise, for example:

i. Each atom is classified in one of a plurality of categories (e.g., 78 categories) based on its neighborhood atoms (CH4, CH3, C aromatic, etc.)
 ii. Vector of fixed length of 156 integers (2*78) as histogram of categories.

The atom type classification system described in Scott A. Wildman, Gordon M. Crippen, *Prediction of Physicochemical Parameters by Atomic Contributions*, J. Chem. Inf. Comput. Sci., 1999, 39, pp. 868-873 is incorporated herein by reference.

An atom class can be defined as an atom species, its properties, and its direct neighbor atom species and properties with their bond types. The encoding of the known reactions 120 can use a sparse vector of atom classes. The number of classes can be extracted by considering all atoms in the known reactions 120 (for example, in the Reaxys database which results in 27,429 classes). Atom classes that occur less than a threshold number of times can be excluded. The threshold number of times can be, for example, 10, 20, 30, 40, 50, 60, 70, 80, 90, etc. . . . , and the like.

Figure 3:
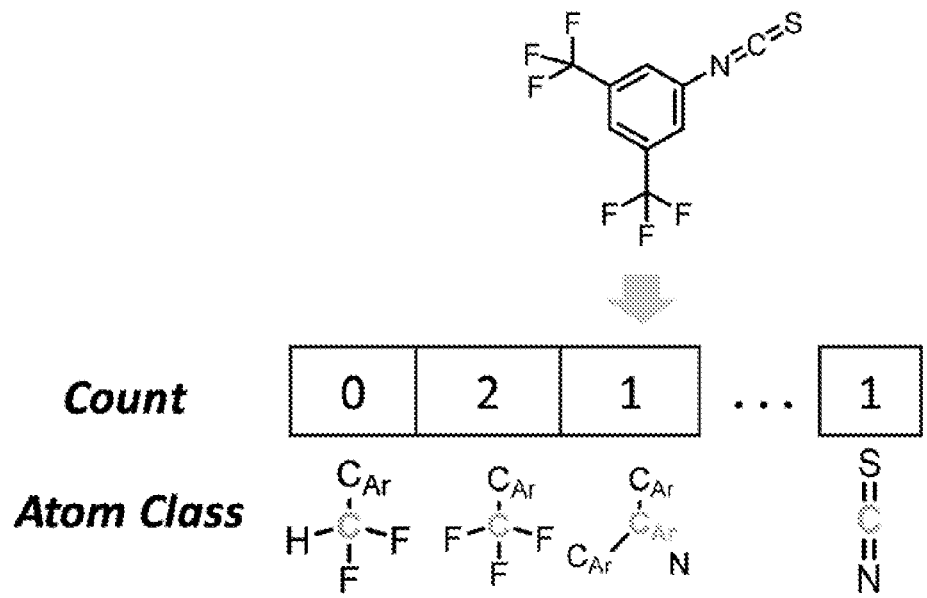
FIG. 3 shows encoding of an example reaction.

FIG. 3 illustrates an example reaction involving MCT type "Isocyanate Reaction with Nucleophile." In this example, a specific instance of a molecule with an isocyanate functional group (1-isothiocyanato-3,5-bis(trifluoromethyl)benzene) is reacted with amine nucleophile (N1,N1-dimethylcyclohexane-1,2-diamine) to give a single product with a thiourea functional group (1-(3,5-bis(trifluoromethyl)phenyl)-3-(2-(dimethylamino)cyclohexyl)thiourea). This specific reaction is encoded as a sparse vector containing a histogram of atom classes present in each of the two reactants as shown. This encoding along with information about the yield and/or reaction conditions can be used as input for the training of a machine learning classifier.

Returning to FIG. 2, at step 220, some or all reactions of the known reactions 120 are defined as positive or negative. Positive examples can be defined as all reactions from the known reactions 120 with a yield greater than a threshold (e.g., 10%, 20% 30%, 40%, 50%, 60%, 70%, 80%, 90%, etc. . . . and the like). Negative examples can be defined as reactions from the known reactions 120 with a yield less than a threshold (e.g., 10%, 20% 30%, 40%, 50%, 60%, 70%, 80%, 90%, etc. . . . and the like) where the reactants are applicable, but the reported product is from a different reaction type.

The encoded reactions, having been identified as positive or negative, can be divided into a training data set and a testing data set. The training data set can be used at 230 to train one or more machine learning classifiers. For example, 80% of the encoded reactions can be used for training and 20% can be used for testing.

In an aspect, a machine learning classifier can be created and trained at 230 for each chemical transformation. The methods and systems described herein may perform step 230 in a variety of ways and contexts. In one example, the methods and systems described herein may train the machine learning-based classifier by, for the training data set, (1) extracting a feature set from the training data set that includes statistically significant features of the positive examples within the training data set and statistically significant features of the negative examples within the training data set and then (2) using the feature set to build a machine learning-based classification model that is capable of indicating whether or not new items of data contain information that falls within the specific category of reactions associated with the training data set.

The term "feature," as used herein, may refer to any characteristic of an item of data that may be used to determine whether the item of data falls within one or more specific categories of chemical reactions. Examples of such features include, without limitation, an aromatic carbon bonded to two other aromatic carbons, a carbon with two bonded hydrogens, an oxygen with a double bond to a carbon, solvent, catalyst, reagent, reaction temperature, reaction time, combinations thereof, and the like.

The methods and systems described herein may extract a feature set from a training data set in a variety of ways. In some examples, a weight may be associated with each extracted feature in order to indicate the relative importance of that feature relative to other features. For example, the methods and systems may (1) determine the frequency of occurrence of various features within both the positive and negative examples within a training data set, (2) rank these positive features and negative features based on, for example, frequency of occurrence, and then (3) select the highest ranked features for inclusion within a feature set. In this example, the weight associated with each feature may be the frequency of occurrence of the specific feature.

As detailed above, after the methods and systems have generated a feature set for a particular training data set, the methods and systems may generate a machine learning-based classification model based on the feature set. The term "machine learning-based classification model," as used herein, may refer to a complex mathematical model for data classification that is generated using machine-learning techniques. In one example, this machine learning-based classifier may include a map of support vectors that represent boundary features. In this example, these boundary features may be selected from, and/or represent the highest-ranked features in, a feature set.

The methods and systems may use the feature sets extracted from training data set to build a machine learning-based classification model (e.g., machine learning classifier) for each of the chemical transformations determined from the encoded reactions 210. In some examples, multiple machine learning-based classification models may be combined into a single machine learning-based classification model. Similarly, a machine learning-based classifier may represent a single classifier containing a single or a plurality of machine learning-based classification models and/or multiple classifiers containing a single or a plurality of machine learning-based classification models.

At 240, the trained machine learning classifier can be tested using the testing data set. A test output of the trained machine learning classifier may be analyzed to assess performance of the trained machine learning classifier. The performance of the trained machine learning classifier can be assessed by a plurality of metrics. By way of example, the performance of the trained machine learning classifier can be assessed by five metrics (TP=True Positive, FP=False Positive, TN=True Negative, and FN=False Negative): 1) Accuracy=(TP+TN)/(TP+FP+FN+TN); 2) Positive Precision=TP/(TP+FP); 3) Negative Precision=TN/(TN+FN); 4) Positive Recall=TP/(TP+FN); and 5) Negative Recall=TN/(TN+FP).

In an aspect, all trained machine learning classifiers may be used, regardless of performance. A trained machine learning classifier, when in use, generates a prediction with a probability of being correct. When in use, a probability value may be selected by the user to accept or reject a classification of a predicted reaction.

Returning to FIG. 1, the trained machine learning classifier(s) may be used to determine the inclusion or exclusion of the predicted reactions 130 in the construction of synthetic routes. A plurality of reactants from the encoded (known) reactions 120 may be input into the trained machine learning classifier(s) which can be configured to assemble the reactants into one or more predicted reactions 130. The trained machine learning classifier(s) may be configured to generate the predicted reactions 130 prior to the route engine 140 receiving input or "on-the-fly" as the route engine 140 determines one or more routes. In an aspect, the trained machine learning classifier(s) may be a part of the route engine 140.

The route engine 140 can receive a target compound (e.g., a user given compound) as input and apply reaction transformations derived from the reactions 110 retrosynthetically to generate one or more synthetic routes 150. The target compound can be any chemical structure and may be input via alphanumeric input and/or a drawn chemical structure. The target compound should be recognized as the compound achieved at the end of one or more chemical reactions.

Figure 4:
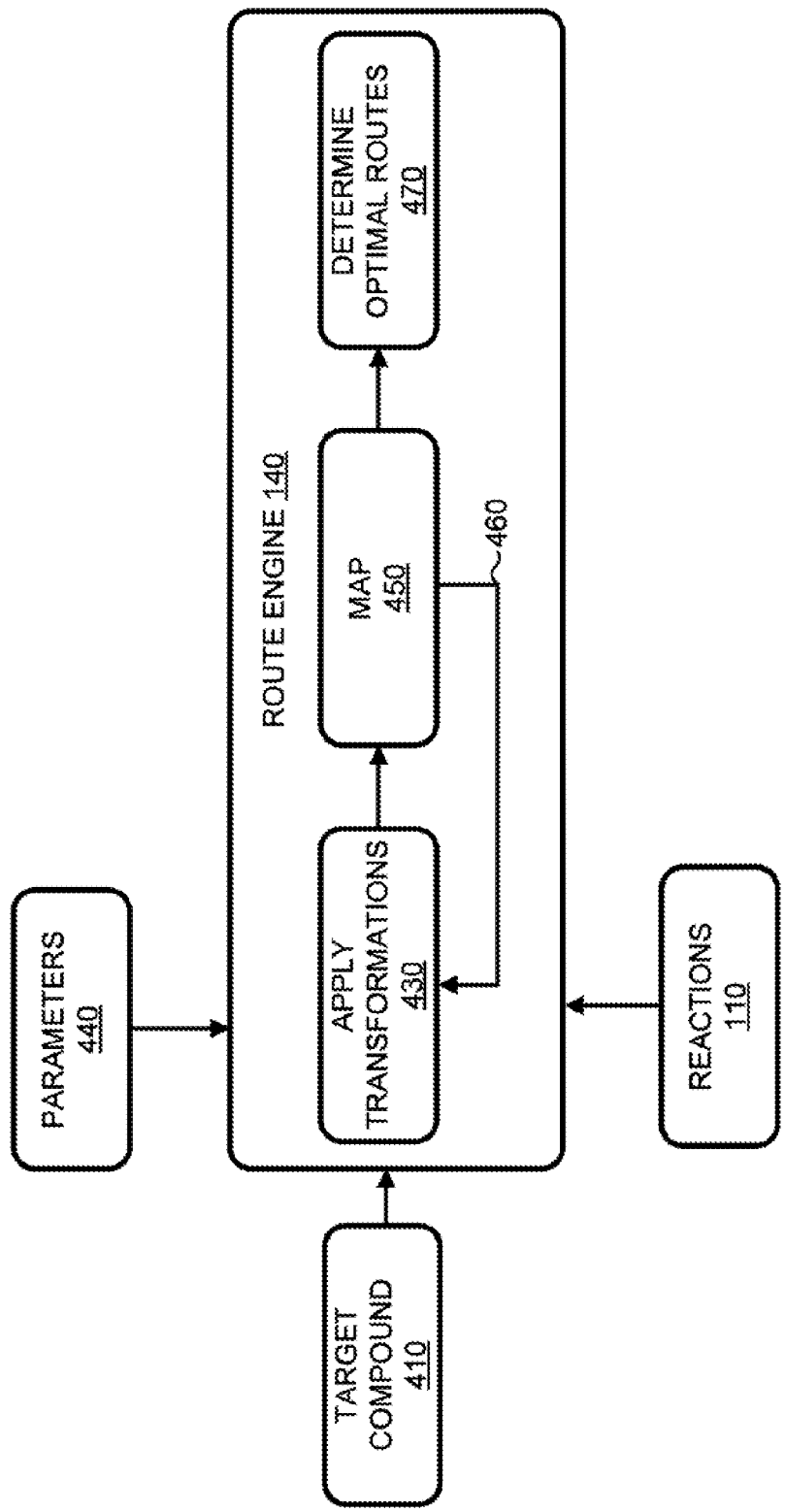
FIG. 4 shows an example process for determining synthetic routes.

As shown in FIG. 4, the route engine 140 can search the reactions 110 (comprised of the known reactions 120 or both the known reactions 120 and the predicted reactions 130, if the predicted reactions 130 have been pre-generated) using a target compound 410 (and/or a downstream/upstream reactant) to identify reactions containing the target compound 410 (and/or the downstream/upstream reactant) and apply reaction transformations retrosynthetically to generate a sequence of potential chemical reactions to produce the target compound 410 (and/or the downstream/upstream reactant). In an aspect, the route engine 140 may apply the target compound 410 (and/or the downstream/upstream reactant) to one or more known reaction transformations (e.g., MCT transformation) at 430 to generate a predicted reaction 130. The route engine 140 may determine whether the target compound 410 contains a minimal structural element (or substructure) specified for the product in one of the general reaction transformations. The predicted reaction 130 may be provided to the one or more machine learning classifiers to assess whether the predicted reaction 130 involving that reagent would be successful. If the prediction is that the predicted reaction 130 would be successful, the predicted reaction 130 can be included in route generation. If the prediction is that the predicted reaction 130 would not be successful, the predicted reaction 130 can be excluded from route generation.

One or more parameters 440 can be specified to modify the application of reaction transformations at 430. The one or more parameters 440 can comprise one or more route modifiers, such as, feedstock data, equipment data (e.g., chemistry apparatus), and the like. The feedstock data can comprise data indicative of available and/or preferred reagents for use in chemical reactions. The equipment data can comprise data indicative of available and/or preferred equipment for use in chemical reactions. The equipment data may be obtained from the modular chemical reaction system described in FIG. 12-FIG. 19 and/or from the apparatus 2000 described in FIG. 20. For example, the equipment data can indicate one or more operational parameters of the modular chemical reaction system or the apparatus 2000. Accordingly, the synthetic routes generated by the methods described herein may be tailored for execution on the modular chemical reaction system or the apparatus 2000, based on the equipment data provided to the route engine 140.

Figure 5:
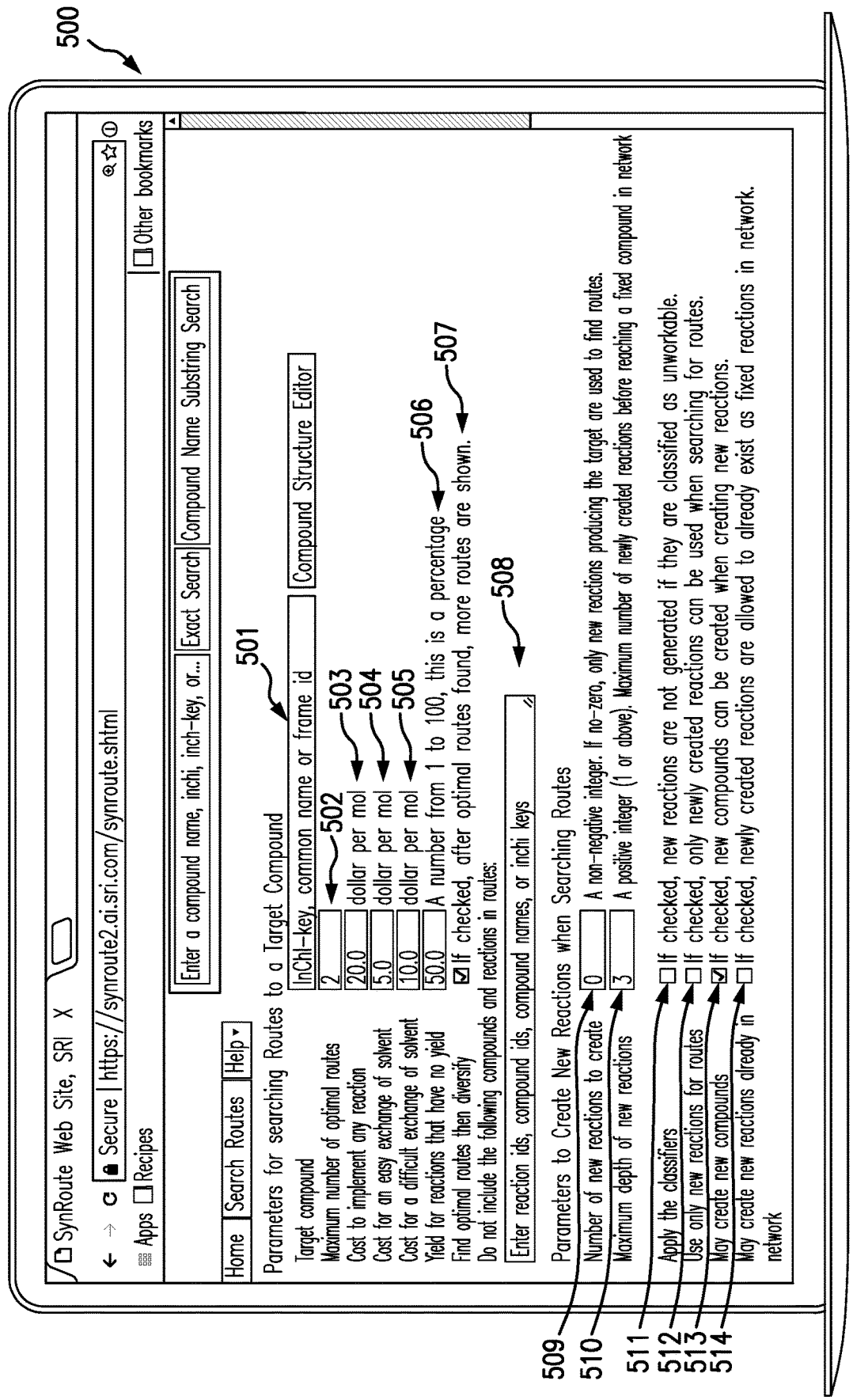
FIG. 5 shows an example user interface.

FIG. 5 provides an example user interface 500 for providing inputs to the route engine 140. The user interface 500 can comprise a user interface element 501 configured to receive the target compound 410, for example as an alphanumeric value indicative of an InChI-key, a common name, a frame id, and/or through the use of a compound structure editor. The user interface 500 can comprise a user interface element 502 configured to receive a maximum number of optimal routes, for example as a numeric value. The user interface 500 can comprise a user interface element 503 configured to receive a cost to implement any reaction, for example as a numeric value indicative of a dollar per mol of a desired compound. The user interface 500 can comprise a user interface element 504 configured to receive a cost for an easy exchange of solvent, for example as a numeric value indicative of a dollar per molar amount of a particular solvent. The user interface 500 can comprise a user interface element 505 configured to receive a cost for a difficult exchange of solvent, for example as a numeric value indicative of a dollar per molar amount of a particular solvent. The user interface 500 can comprise a user interface element 506 configured to receive a yield for reactions that have no yield, for example as a numeric value indicative of a percent yield. The user interface 500 can comprise a user interface element 506 configured to receive an indication that, after optimal routes are found, more routes should be shown, for example as a binary indication (e.g., a checkbox). The user interface 500 can comprise a user interface element 508 configured to receive a compounds (reactants) to exclude from consideration, for example as for example as an alphanumeric value indicative of a reaction id, a compound id, a compound name, or an inchi key. The user interface 500 can comprise a user interface element 509 configured to receive a number of new reactions to create, for example as a numeric value. The user interface 500 can comprise a user interface element 510 configured to receive maximum depth of new reactions, for example as a numeric value. The user interface 500 can comprise a user interface element 511 configured to receive an indication to apply the machine learning classifiers, for example as a binary indication (e.g., a checkbox). The user interface 500 can comprise a user interface element 512 configured to receive an indication use only new reactions for routes, for example as a binary indication (e.g., a checkbox). The user interface 500 can comprise a user interface element 513 configured to receive an indication as to whether the route engine 140 should create new compounds, for example as a binary indication (e.g., a checkbox). The user interface 500 can comprise a user interface element 514 configured to receive an indication as to whether the route engine 140 should create new reactions already in network, for example as a binary indication (e.g., a checkbox).

Returning to FIG. 4, at 450, the route engine 140 can map the generated reactants from the sequence of potential chemical reactions into a fixed reaction network using the Morgan Algorithm. The Morgan algorithm creates a unique name (or code) for each compound of a reaction, from which it can be determined if each compound already exists in the fixed reaction network. The Morgan algorithm classifies congeneric atoms of a compound and selects invariant-labeled atoms. The classification uses the concept of considering the number of neighbors of an atom (connectivity), and does so in an iterative manner (extended connectivity). On the basis of certain rules, the Morgan Algorithm produces an unambiguous and unique numbering of a compound in a network (e.g., a generated reactant).

At 460, for each compound (as reactant) one reaction away from the target compound 410 (and/or the downstream/upstream reactant), steps 430 and 450 can be repeated until a maximum number of new reactions is reached, building a route network with each new route. By way of example, the maximum number of new reactions can be ≤100 k, ≤200 k, ≤300 k, ≤400 k, ≤500 k, ≤600 k, ≤700 k, ≤800 k, ≤900 k, ≤1000 k, and the like. The route engine can thus generate one or more sequences of chemical reactions designed to result in the creation of the target compound 410. The sequence of chemical reactions may be referred to as a route. The route network for a target compound 410 may be represented in a tree data structure and output for display.

Figure 6:
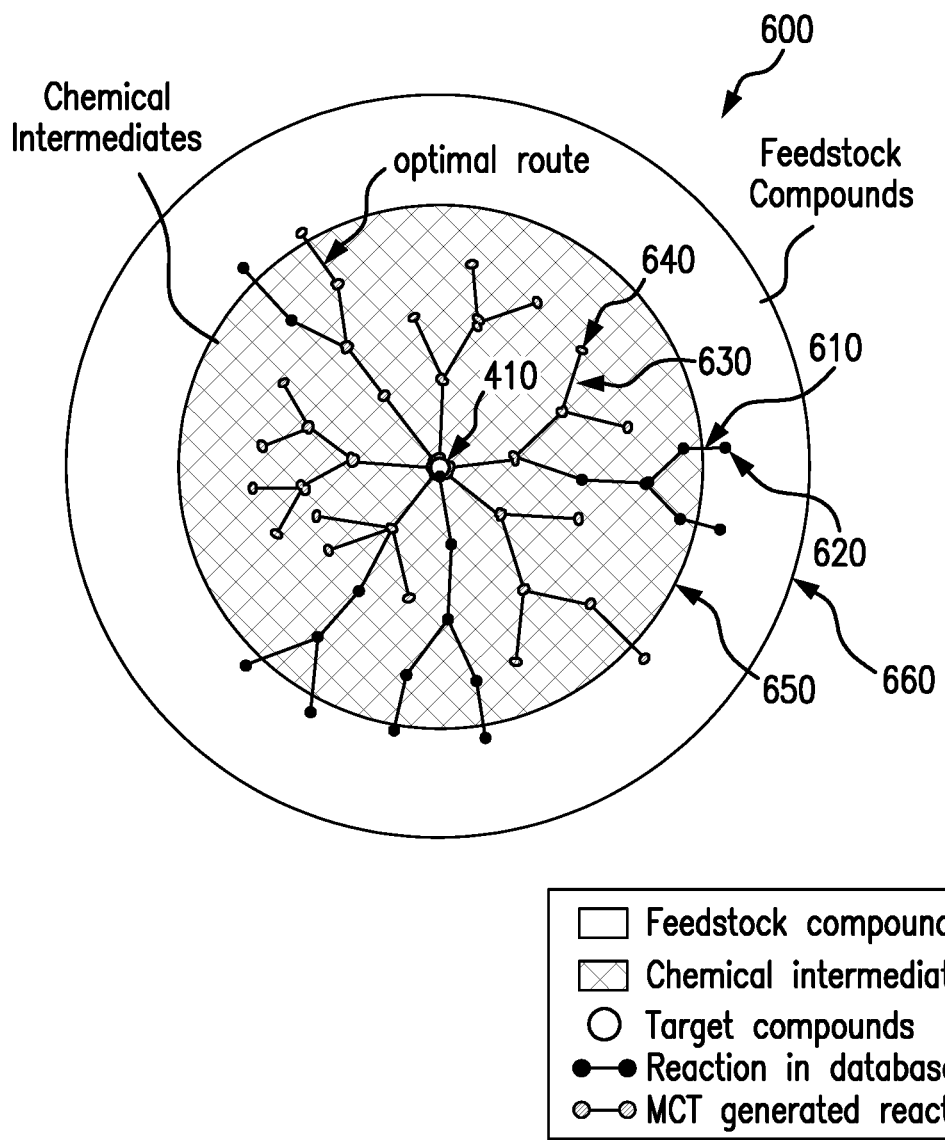
FIG. 6 shows a plurality of synthetic routes in a tree data structure.

FIG. 6, shows an example tree data structure 600 comprised of a plurality of routes. The target compound 410 may be positioned at the center of the tree data structure 600. Each edge may comprise a reaction and each node may comprise a compound (reactant). As shown, an edge 610 represents a reaction derived from the known reactions 120 and a node 620 represents a compound (reactant) involved in the reaction of edge 610. An edge 630 represents a reaction derived from the predicted reactions 130 and a node 640 represents a compound (reactant) involved in the reaction of edge 630. Nodes contained within an area 650 represent chemical intermediates, whereas nodes contained within an area 660 represent purchasable feedstock compounds. Thus, the nodes within the area 660 may serve as the initial compounds in a series of chemical reactions that will trace a route (series of chemical reactions) to the starting (target) compound 410.

Returning to FIG. 4, once a maximum number of reactions created retrosynthetically from the target compound 410 is reached, the route engine 140 can determine optimal routes at 470. The route engine 140 can utilize fast searching of the route network to determine optimal routes using a Dijkstra-like algorithm.

The route engine 140 can determine optimal routes at 470 according to a two-stage approach. In the first stage, the route engine 140 can determine compounds that could produce the target compound in k reactions or less (at most k reactions). In the second stage, the route engine 140 can determine minimum-cost routes to the target compound 410. A route having a lowest minimum cost may be identified as the optimal route. A plurality of routes having costs below a threshold may be identified as optimal routes. The second stage can determine the optimal route without considering reaction telescoping. Telescoping of reactions occurs when two or more reactions in appear in a reaction sequence without work-up or solvent exchange steps.

Figure 7:
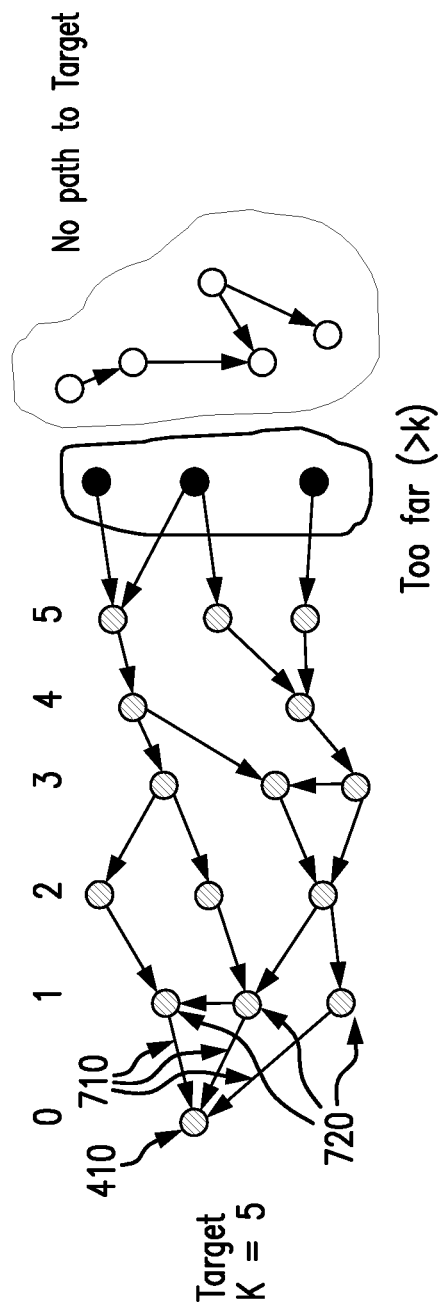
FIG. 7 shows an example of synthetic route selection.

As shown in FIG. 7, in the first stage, the route engine 140 can start with the starting (target) compound and identify the chemical reactions 710 that produce the target compound 410. The route engine 140 can determine the reactants 720 of these reactions 710 and tag the reactants 720 at distance of 1 to the target compound 410. The route engine 140 can repeat the process from the reactants 720, by determining the reactions that produce the reactants 720, determine the reactants of those reactions, and tag those reactants at a distance of 2 to the target compound 410. This process can repeat, tagging each reactant until reaching a distance k from the target compound 410. Every reactant is tagged only once until reaching a distance k. Reactions and reactants with no path to the target compound 410 are excluded from consideration. Reactions and reactants beyond k are excluded from consideration. Stage one can be used to limit the feedstocks and reactions to consider.

Figure 8:
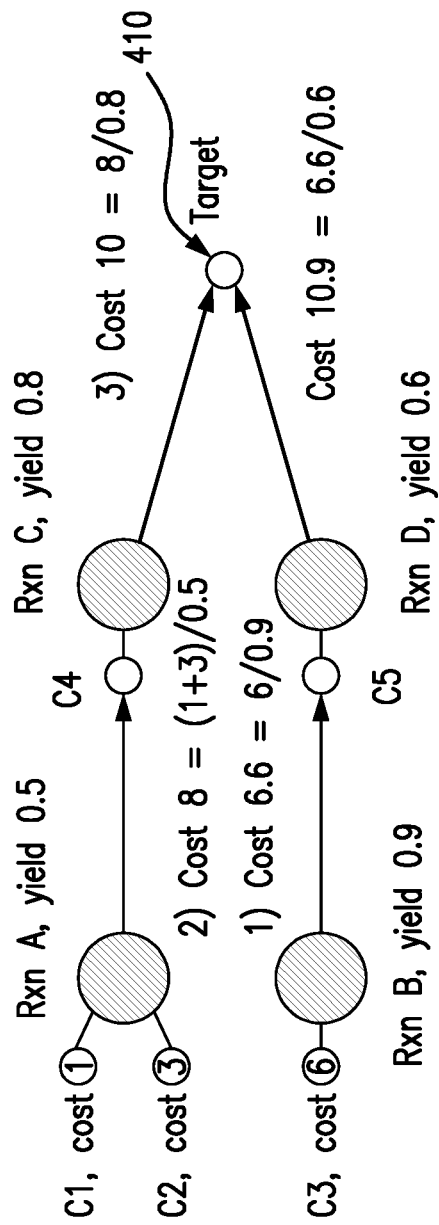
FIG. 8 shows an example application of a cost function for synthetic route selection.

As shown in FIG. 8, in the second stage, the route engine 140 can determine minimum-cost routes. The route engine 140 can initialize a priority queue with reactions that can activate from feedstocks. A reaction can activate if all reactants necessary for the reaction are feedstocks. A reaction cost can be determined as the sum of the feedstock costs divided by the yield. The route engine 140 can determine an active reaction with the minimum cost and identify the next reactions that are activated by products of the active reaction with the minimum cost. The next reactions can be added to the priority queue and the process can be repeated until the target compound 410 is reached. Each reaction is only considered once. As shown in FIG. 8 Reaction A, Reaction B, Reaction C. and Reaction D each utilize feedstocks for reactants. Reaction A utilizes reactants C1 and C2. Reactant C1 has a determined cost of 1 and Reactant C2 has a determined cost of 3. The yield for Reaction A is 0.5. The total cost of Reaction A is determined by (1+3)/0.5, resulting in a cost of 8. The next reaction after Reaction A is Reaction C. Reaction C utilizes reactant C4. Reactant C4 has a determined cost of 8. The yield for Reaction C is 0.8. The total cost of Reaction C is determined by 8/0.8, resulting in a cost of 10. The result of Reaction C is the starting (target) compound 410. The total cost for the route Reaction A-Reaction C is 8+10=18.

Reaction B utilizes reactant C3. Reactant C3 has a determined cost of 6. The yield for Reaction B is 0.9. The total cost of Reaction B is determined by 6/0.9, resulting in a cost of 6.6. The next reaction after Reaction B is Reaction D. Reaction D utilizes reactant C5. Reactant C5 has a determined cost of 6.6. The yield for Reaction D is 0.6. The total cost of Reaction D is determined by 6.6/0.6, resulting in a cost of 10.9. The result of Reaction D is the starting (target) compound 410. The total cost for the route Reaction B-Reaction D is 6.6+10.9=17.5. At stage two, the route engine 140 can compare the total costs and select the route having the lowest cost. As shown in FIG. 8, the route Reaction B-Reaction D has a lower cost (17.5) than Reaction A-Reaction C (18). Thus, the route engine 140 can determine the route Reaction B-Reaction D as the minimal cost route.

The route engine 140 can determine cost of a route in a variety of ways. The cost of a route can be the financial (e.g., monetary) cost of producing the starting (target) compound 410, which is the cost of the reaction producing the starting (target) compound 410, plus the sum of all solvent exchange costs (e.g., all costs in dollars per mol). The cost of a reaction can be the sum of the financial (e.g., monetary) costs of the reactants, including reagents, divided by the yield of the reaction, plus a fixed financial (e.g., monetary) cost to implement the reaction. The financial (e.g., monetary) cost of a solvent exchange, between two reactions or in stages of a reaction, can be a fixed cost. The route(s) having the minimal cost can be identified as the optimal route(s).

In an aspect, the route engine 140 can determine cost according to the following formula:

$$\text{Cost}(C_R) = ICost(R) + \left( \sum_{C \in Reactants(R)} \text{Cost}(C_{R_i}) + \sum_{f \in Feedstocks(R)} f_{cost} \right) / R_{yield}$$

where
$C_R$ is a compound C produced by reaction R
$ICost(R)$ is a fixed cost to implement reaction R
$C_{R_i}$ is a reactant of R produced by some reaction $R_i$
$f_{cost}$ is a fixed cost for feedstock f
$R_{yield}$ is the yield of reaction R, $0 < R_{yield} \leq 1$ Returning to FIG. 1, the optimal routes determined by the route engine 140 can be identified as optimal synthetic routes 150 and output, either graphically comprehensible to chemists, as a tree of reactions described textually with the names of the compounds or in a computational schema using common exchange formats such as JavaScript Object Notation (JSON) or extensible markup language (XML).

Figure 9A:
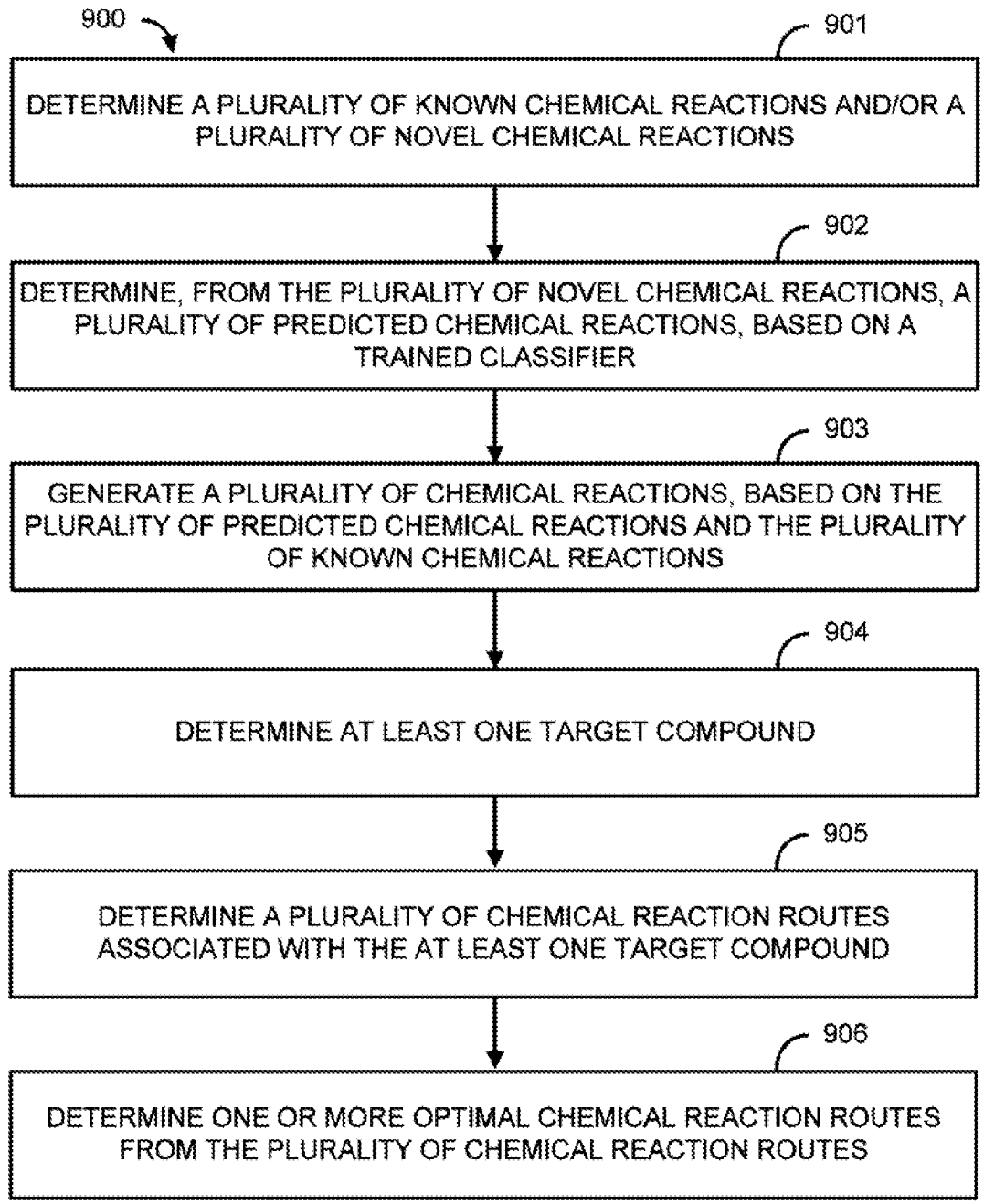
FIG. 9A shows an example method.

FIG. 9A shows a computational method 900 for identifying one or more existing or novel chemical synthesis routes for producing a target compound comprising determining a plurality of known chemical reactions and/or a plurality of novel chemical reactions at 901. The plurality of novel reactions may be extrapolated from generalized known chemical transformations.

The method 900 may comprise determining, from the plurality of novel chemical reactions, a plurality of predicted chemical reactions, based on a trained classifier at 902. The trained classifier may be trained on data derived from a plurality of chemical reactions known to be successful and a plurality of chemical reactions known to be unsuccessful that are instances of a given chemical transformation.

The method 900 may comprise generating a plurality of chemical reactions, based on the plurality of predicted chemical reactions and the plurality of known chemical reactions at 903. Each chemical transition of the plurality of chemical reactions may represent a transformation of one compound to another compound.

The method 900 may comprise determining at least one target compound at 904.

The method 900 may comprise determining a plurality of chemical reaction routes associated with the at least one target compound at 905. Each chemical reaction route may comprise one or more chemical reactions of the plurality of chemical reactions that produces the target compound.

The method 900 may comprise determining one or more optimal chemical reaction routes from the plurality of chemical reaction routes identified for producing the target compound at 906. At least one of the one or more optimal chemical reaction routes may comprise at least one known reaction transformation and at least one predicted reaction transformation.

The method 900 may further comprise training a classifier on a training data set, wherein the training data set comprises one or more of, a chemical reaction database, estimated yields, or predicted yields for the one or more chemical reactions. Training the classifier on the training data set may comprise receiving a dataset comprising one or more chemical reactions based on one or more chemical transformations, wherein each of the one or more chemical reactions comprises at least one reactant, wherein each reactant is comprised of one or more atoms. For each reactant, the method 900 may classify the one or more atoms into a category based on a neighborhood atom, a bond order, and/or a number of hydrogen atoms present. For each reactant, the method 900 may determine a vector based on a histogram of categories. The method 900 may determine a training dataset comprised of a) vectors of reactions associated with a specific transformation and b) vectors of reactions associated with the specific transformation but yield a product from a different reaction type, expose a classifier to a portion of the training dataset to train the classifier, and expose the trained classifier to another portion of the training dataset to test the trained classifier.

Exposing the trained classifier to another portion of the training dataset to test the trained classifier may comprise assessing performance of the trained classifier based on one or more metrics. The one or more metrics may comprise one or more of accuracy, positive precision, negative precision, positive recall, or negative recall.

The method 900 may further comprise generating a tree data structure, wherein the target compound is a root node of the tree data structure. The method 900 may further comprise adding, to the tree data structure, a plurality of branches, wherein each branch of the plurality of branches comprises a synthetic route of the plurality of synthetic routes.

Determining a plurality of synthetic routes associated with the target compound may be based on one or more parameters. The one or more parameters may comprise one or more of available feedstock, available chemical substances, or available equipment.

Determining the one or more optimal synthetic routes from the plurality of synthetic routes may be based on one or more parameters. The one or more parameters comprise one or more of available feedstock, available chemical substances, available equipment, yield, financial cost, time, reaction conditions, or likelihood of reaction success. Determining the one or more optimal synthetic routes from the plurality of synthetic routes may comprise determining all compounds that can reach the target in at most a pre-defined number of steps and determining a minimal cost synthetic route to the target compound without considering transition telescoping.

Figure 9B:
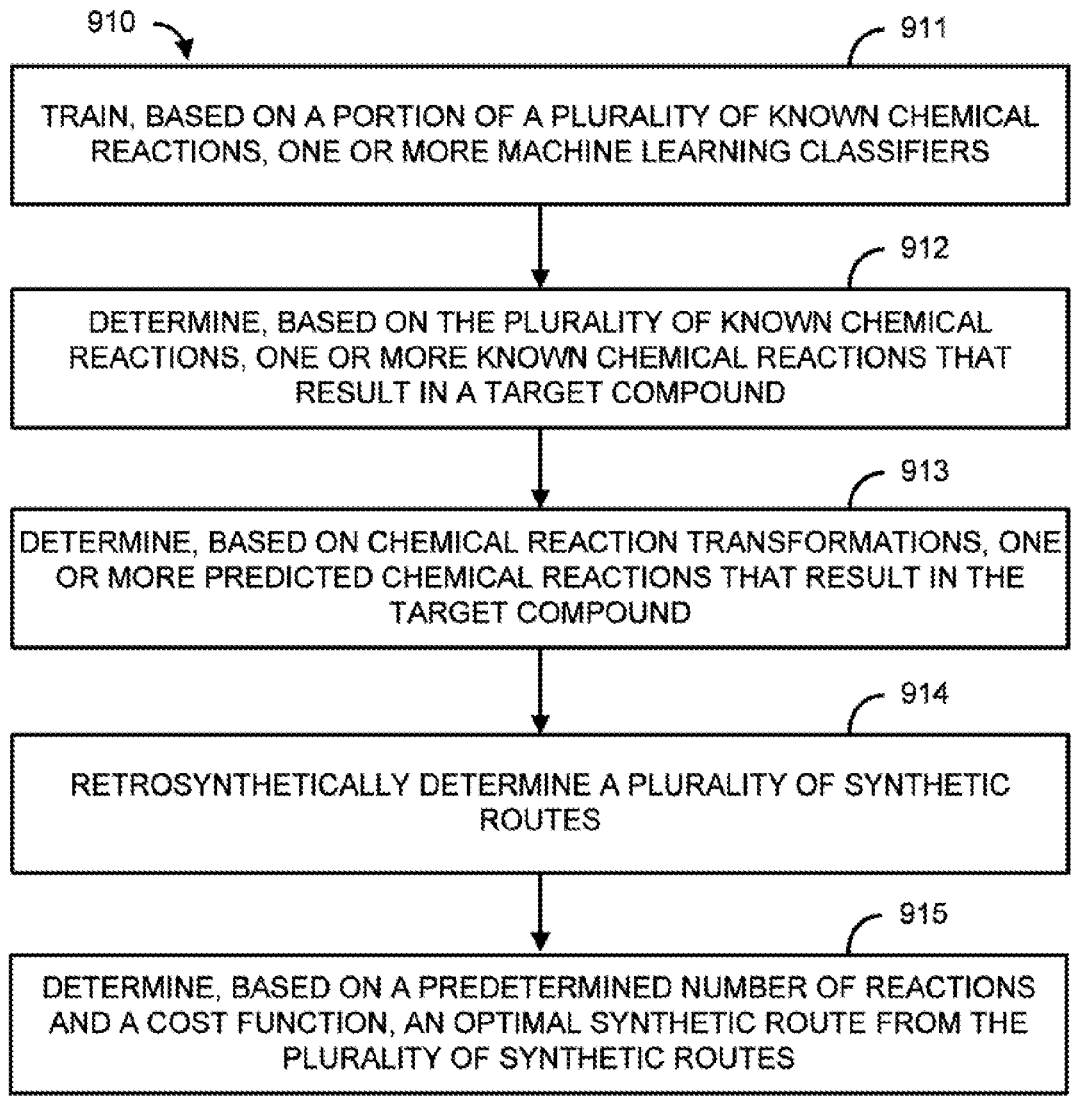
FIG. 9B shows an example method.

Determining the minimal cost route may comprise evaluating a cost function. The cost function may comprise $$\text{Cost}(C_R) = I\text{Cost}(R) + \left( \sum_{C \in \text{Reactants}(R)} \text{Cost}(C_{R_i}) + \sum_{f \in \text{Feedstocks}(R)} f_{cost} \right) / R_{yield}$$

where
$C_R$ is a compound C produced by reaction R
$I\text{Cost}(R)$ is a fixed cost to implement reaction R
$C_{R_i}$ is a reactant of R produced by some reaction $R_i$
$f_{cost}$ is a fixed cost for feedstock f
$R_{yield}$ is the yield of reaction R, $0 < R_{yield} \leq 1$ FIG. 9B shows a method 910 for identifying one or more synthetic routes for synthesizing a target compound comprising training, based on a portion of a plurality of known chemical reactions, one or more machine learning classifiers at 911. The plurality of known chemical reactions may be derived from one or more of, a chemical reaction database, estimated yields, or predicted yields for the one or more chemical reactions. Training, based on a portion of a plurality of known chemical reactions, one or more machine learning classifiers may comprise receiving a dataset comprising one or more chemical reactions based on one or more chemical transformations, wherein each of the one or more chemical reactions comprises at least one reactant, wherein each reactant is comprised of one or more atoms, for each reactant, classifying the one or more atoms into a category based on a neighborhood atom, a bond order, and/or a number of hydrogen atoms present, for each reactant, determining a vector based on a histogram of categories, determining a training dataset comprised of a) vectors of reactions associated with a specific transformation and b) vectors of reactions associated with the specific transformation but yield a product from a different reaction type, exposing a classifier to a portion of the training dataset to train the classifier, and exposing the trained classifier to another portion of the training dataset to test the trained classifier. Exposing the trained classifier to another portion of the training dataset to test the trained classifier may comprise assessing performance of the trained classifier based on one or more metrics. The one or more metrics may comprise one or more of accuracy, positive precision, negative precision, positive recall, or negative recall.

The method 910 can comprise determining, based on the plurality of known chemical reactions, one or more known chemical reactions that result in a target compound at 912.

The method 910 can comprise determining, based on chemical reaction transformations, one or more predicted chemical reactions that result in the target compound at 913. The one or more predicted chemical reactions may be predicted as being successful by the one more machine learning classifiers The method 910 can comprise retrosynthetically determining a plurality of synthetic routes at 914. Each synthetic route may result in the target compound, wherein at least one synthetic route comprises at least one of the one or more known chemical reactions and at least one of the one or more predicted chemical reactions. Retrosynthetically determining a plurality of synthetic routes may be based on one or more parameters. The one or more parameters may comprise one or more of available feedstock, available chemical substances, or available equipment.

The method 910 can comprise determining, based on a predetermined number of reactions and a cost function, an optimal synthetic route from the plurality of synthetic routes at 915. Determining, based on a predetermined number of reactions and a cost function, an optimal synthetic route from the plurality of synthetic routes may be further based on one or more parameters. The one or more parameters comprise one or more of available feedstock, available chemical substances, available equipment, yield, financial cost, time, reaction conditions, or likelihood of reaction success. Determining, based on a predetermined number of reactions and a cost function, an optimal synthetic route from the plurality of synthetic routes may comprise determining all compounds that can reach the target in at most a pre-defined number of steps and determining a minimal cost synthetic route to the target compound without considering transition telescoping. The cost function may comprise:

$$\text{Cost}(C_R) = I\text{Cost}(R) + \left( \sum_{C \in \text{Reactants}(R)} \text{Cost}(C_{R_i}) + \sum_{f \in \text{Feedstocks}(R)} f_{cost} \right) / R_{yield}$$

where
$C_R$ is a compound C produced by reaction R
$I\text{Cost}(R)$ is a fixed cost to implement reaction R
$C_{R_i}$ is a reactant of R produced by some reaction $R_i$
$f_{cost}$ is a fixed cost for feedstock f
$R_{yield}$ is the yield of reaction R, $0 < R_{yield} \leq 1$ The method 910 may further comprise generating a tree data structure, wherein the target compound is a root node of the tree data structure. The method 910 may further comprise adding, to the tree data structure, a plurality of branches, wherein each branch of the plurality of branches comprises a synthetic route of the plurality of synthetic routes.

Figure 10:
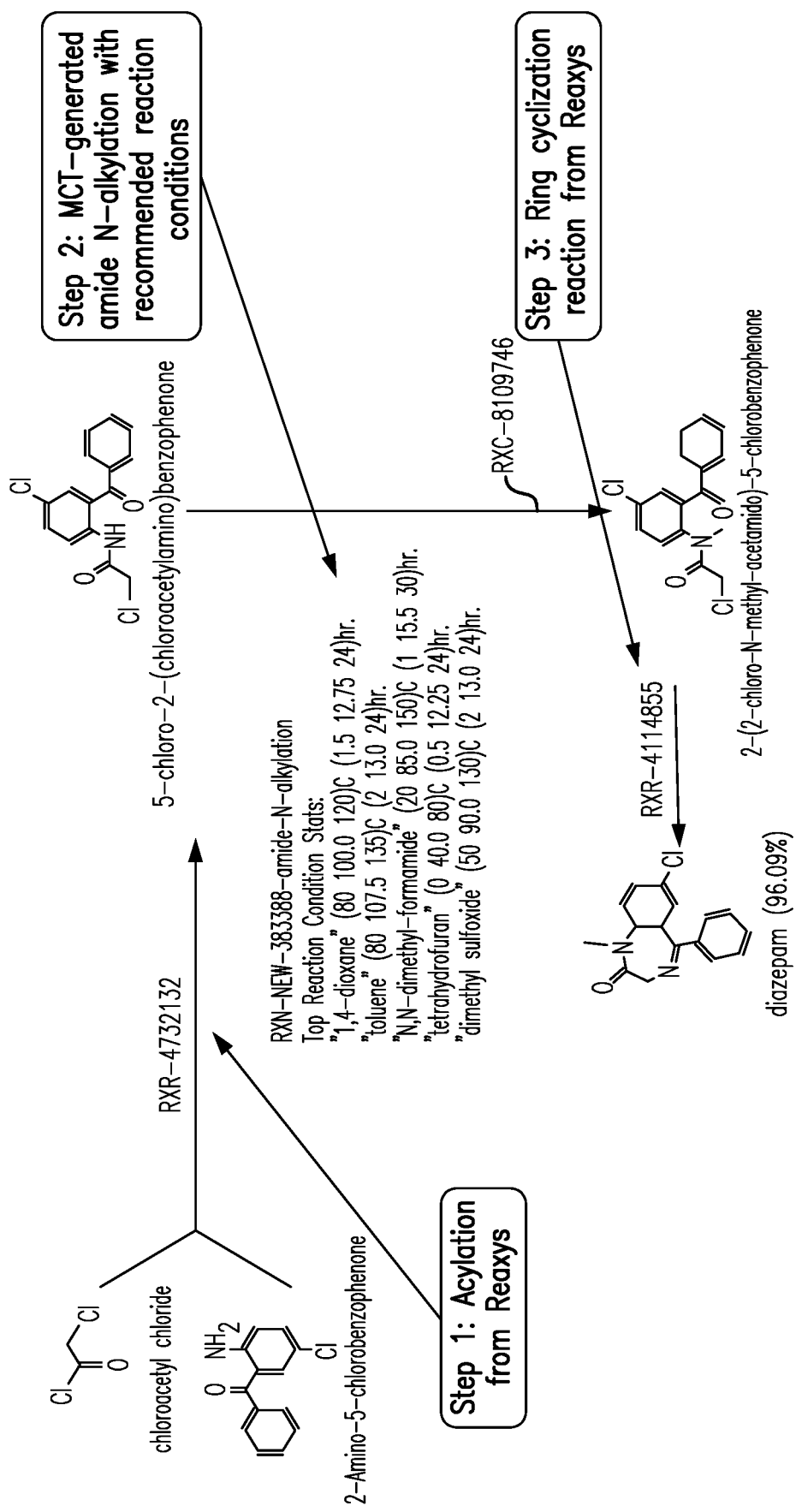
FIG. 10 shows an example synthetic route generated using the described methods.

FIG. 10 shows a route for creating Diazepam derived from the methods and systems described. An optimal route generated without utilization of the machine learning classifiers to classify predicted reactions results in the well-known two-step synthesis route contained in the Reaxys database. The route illustrated in FIG. 10 was generated using the methods and systems described utilizing the machine learning classifiers. As shown, the first step of the optimal route is the acylation of 2-amino-5-chlorobenzophenone, resulting in 5-chloro-2-(chloroacetylamino)benzophenone. The reaction of the first step was obtained from known reactions (e.g., Reaxys). The second step of the optimal route is an amide N-alkylation with recommended reaction conditions that was generated by the route engine 140 and determined by a trained machine learning classifier as being successful. The result of the second reaction is 2-(2-chloro-N-methyl-acetamide)-5-chlorobenzophenone. The third step of the optimal route is a ring cyclization reaction which results in Diazepam. The reaction of the third step was obtained from known reactions (e.g., Reaxys). The route was executed on a multi-step flow synthesizer, affording Diazepam in 78% yield on 161 mg scale.

Figure 11:
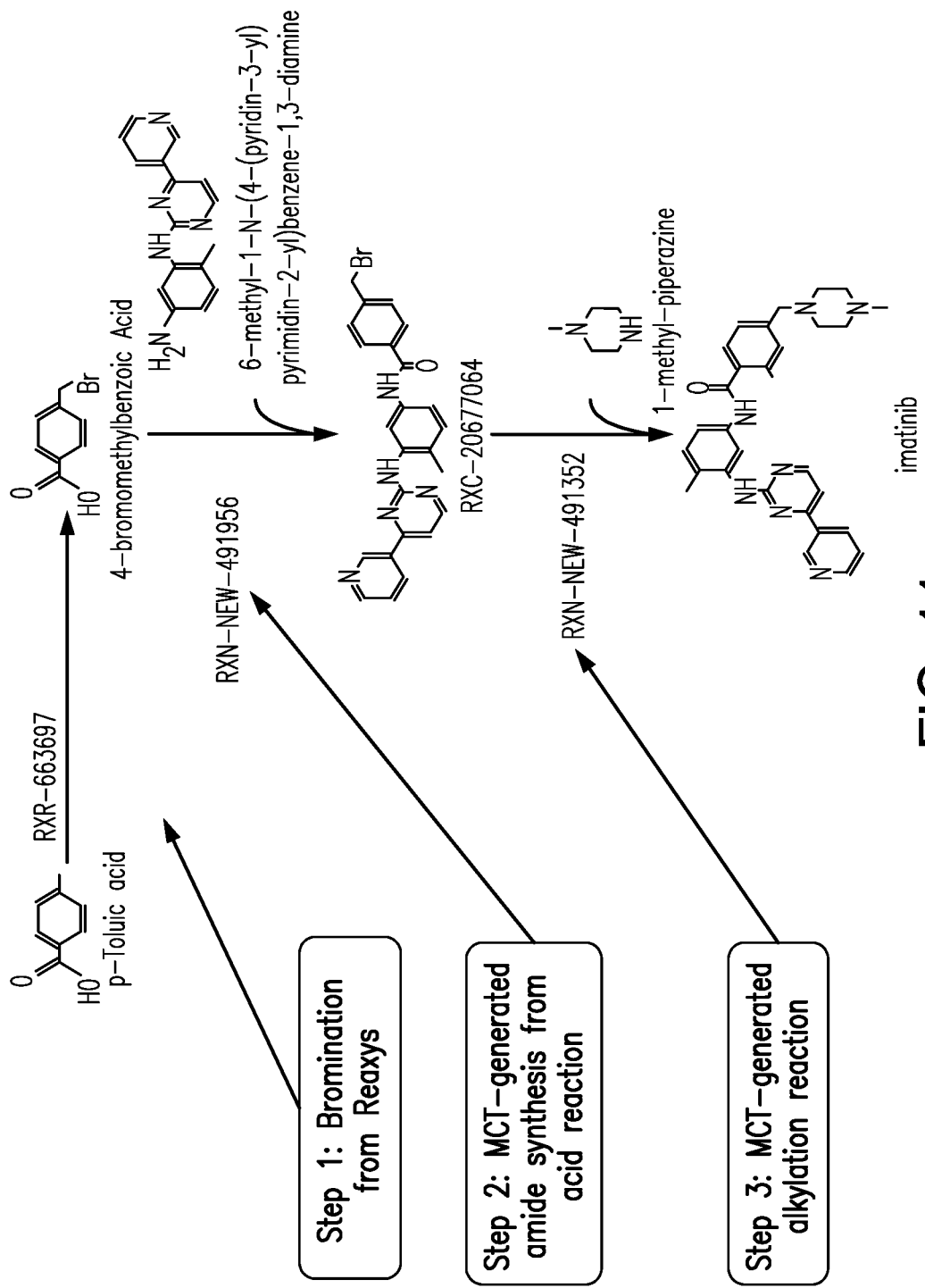
FIG. 11 shows an example synthetic route generated using the described methods.

FIG. 11 shows a route for creating Imatinib derived from the methods and systems described. The route illustrated in FIG. 10 was generated using the methods and systems described utilizing the machine learning classifiers. As shown, the first step of the optimal route is the bromination of p-toluic acid, resulting in 4-bromomethylbenzoic acid. The reaction of the first step was obtained from known reactions (e.g., Reaxys). The second step of the optimal route is an amide synthesis from an acid reaction that was generated by the route engine 140 and determined by a trained machine learning classifier as being successful. The result of the second reaction is 4-(bromomethyl)-N-(4-methyl-3-((4-(pyridin-3-yl)pyrimidin-2-yl)amino)phenyl) benzamide. The third step of the optimal route is an alkylation reaction which results in Imatinib. The reaction of the third step was generated by the route engine 140 and determined by a trained machine learning classifier as being successful. The route was executed on a multi-step flow synthesizer, affording Imatinib in 91% yield on 8.4 g scale.

Disclosed herein, in various aspects and with reference to FIG. 12-FIG. 19, is a modular chemical reaction system 10. The full disclosure of this apparatus can be found in PCT/US2018/026557, filed on Apr. 6, 2018, entitled, "Modular Systems For Performing Multistep Chemical Reactions, And Methods Of Using Same," the contents of which are incorporated by reference here in its entirety. The system 10 can have a substrate layer 20 and a surface-mount layer 40 including a plurality of modules 50 as further disclosed herein. The system 10 can further comprise a plurality of sealing elements 90.

Figure 12:
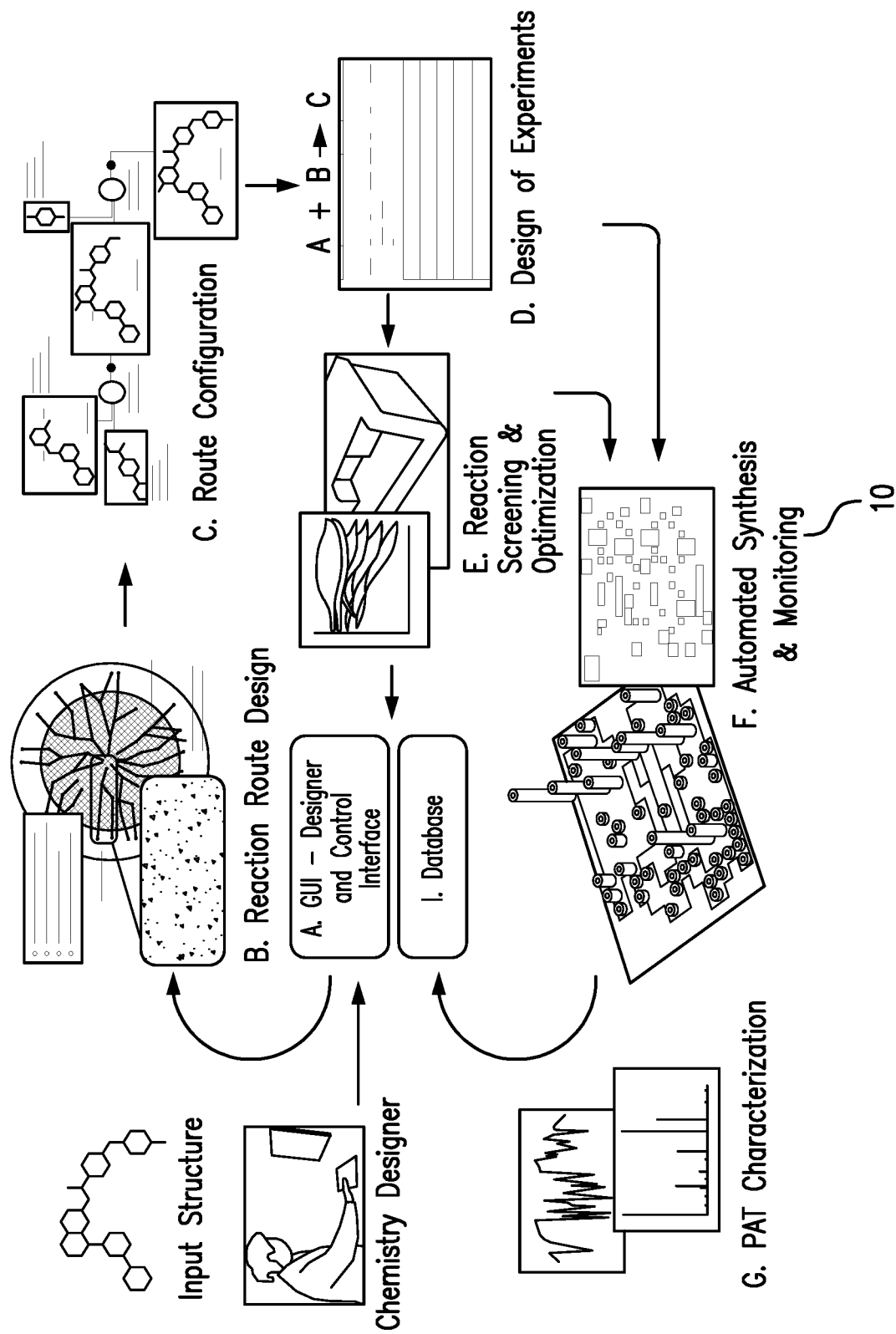
FIG. 12 is a schematic diagram depicting the relationship of the modular reaction systems and methods disclosed herein to an overall process for designing, performing, analyzing, and modifying chemical reactions.

In use, and as schematically depicted in FIG. 12, it is contemplated that the modular chemical reaction system 10 can provide automated chemical synthesis and monitoring capabilities that can be incorporated into a comprehensive system for designing, simulating, screening, performing, analyzing, and modifying/optimizing chemical reactions. As further disclosed herein, it is contemplated that the disclosed system 10 can provide modularity that permits rapid reconfiguration (optionally, rearrangement) of system components to quickly change fluid flow pathways associated with multiple, varying reactions. In some aspects, reconfiguration means selecting alternative pathways within the system having defined pathways and pre-positioned modules and/or analysis devices. In these aspects, it is contemplated that the defined pathways can be separated by valve modules as disclosed herein, which can be adjusted to modify the flow of fluid within and among the defined pathways. In other aspects, reconfiguration can include physically adding new modules or analysis devices to the disclosed system 10. Additionally, or alternatively, reconfiguration can include removing or replacing at least one module or analysis device as disclosed herein. It is further contemplated that the disclosed system 10 can provide a framework for performing multiple chemical reactions using a single configuration of reaction modules. Still further, it is contemplated that the disclosed system 10 can provide monitoring capabilities during the performance of a chemical reaction that have previously been unachievable. Still further, it is contemplated that the disclosed system 10 can control and/or optimize reaction conditions based on feedback received from various modules and analysis devices as a reaction occurs.

In exemplary aspects, and with reference to FIGS. 13-16, the substrate layer 20 can have a substrate 22 and a plurality of flow components (e.g., flow connectors 26) positioned within the substrate. In these aspects, the substrate 22 can have an outer surface 24. Optionally, in exemplary aspects, the substrate 22 can comprise a plurality of substrate bodies that are selectively positioned in parallel to establish a framework for parallel fluid passageways as disclosed herein. Although the substrate bodies are generally described herein as being in parallel, it is contemplated that the substrate bodies can be positioned in any desired configuration, including perpendicular and angled configurations. Alternatively, it is contemplated that the substrate 22 can be a single contiguous platform structure. In exemplary aspects, the substrate layer 20 (and the manifold layer disclosed further herein) can be configured for selective attachment to an underlying grid support structure defining a plurality of openings for receipt of fasteners to secure the substrate layer and/or manifold layer to the grid support structure.

Figure 13:
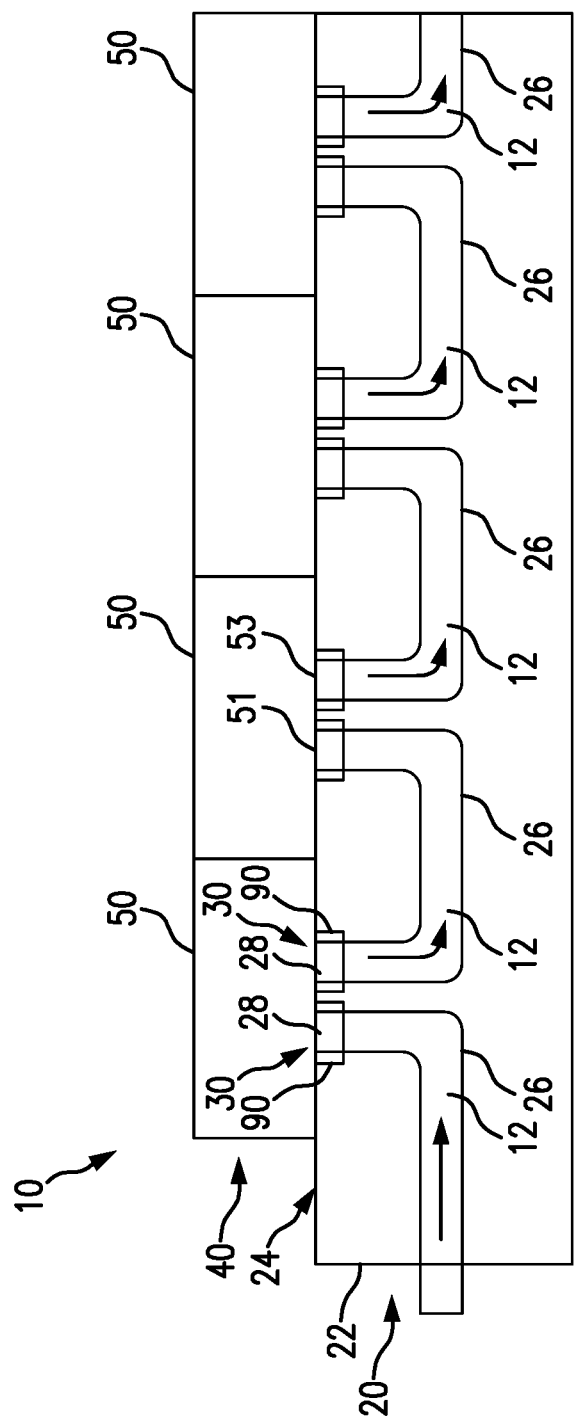
FIG. 13 is a schematic diagram of a portion of an exemplary reaction system having a plurality of modules surface-mounted to a substrate layer as disclosed herein.

Optionally, each module 50 of the plurality of modules can have at least a first inlet 51 and a first outlet 53 as depicted in FIG. 13. However, it is contemplated that some modules can be configured for storage of material and/or otherwise only include an inlet 51 or an outlet 53.

In additional aspects, the plurality of modules 50 of the surface-mount layer 40 can be selectively mounted to the outer surface 24 (e.g., upper surface) of the substrate 22 in overlying relation to the plurality of flow components (e.g., flow connectors 26). In these aspects, it is contemplated that the plurality of modules 50 can include a plurality of flow modules 52 that receive fluid that forms a portion of a fluid flow pathway within the system 10. It is further contemplated that each flow module 52 of the plurality of flow modules can be positioned in fluid communication with at least one flow component (e.g., flow connector 26) of the plurality of flow components at a respective interface 30 as shown in FIG. 13. In further aspects, the plurality of sealing elements 90 can be configured to establish a fluid-tight seal at each interface 30 between a flow module 52 of the plurality of flow modules and a flow component (e.g., flow connector 26) of the plurality of flow components. As further disclosed herein, at least a portion of the plurality of flow modules 52 and at least a portion of the plurality of flow components (e.g., flow connectors 26) can cooperate to establish a fluid flow pathway 12 (e.g., a first fluid flow pathway) for performing at least one step of a chemical reaction or series of chemical reactions. As further disclosed herein, it is contemplated that the configuration of the flow modules and flow components can be selectively modified to produce a second fluid flow pathway that differs from the first fluid flow pathway. Optionally, in exemplary aspects, the fluid flow pathway can be a liquid flow pathway. In these aspects, it is contemplated that the sealing elements 90 can be configured to establish liquid-tight seals at each interface between a flow module 52 and a flow connector 26. In further exemplary aspects, it is contemplated that the chemical reaction can be a continuous flow, multi-step chemical reaction.

Figure 16:
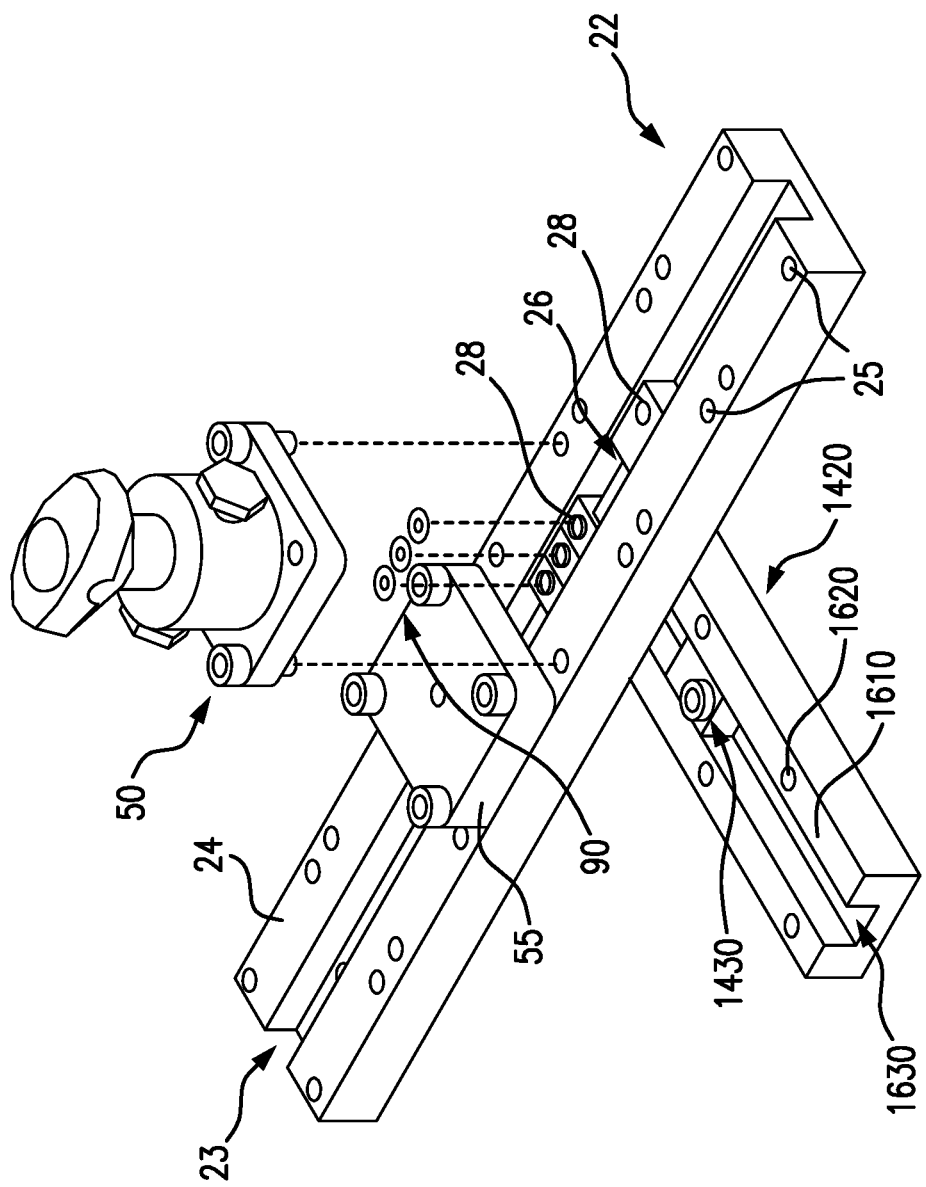
FIG. 16 is a perspective view depicting the interaction between exemplary surface-mount components, flow connectors, and substrate and manifold layers as disclosed herein.

In additional aspects, each flow connector 26 can be configured to selectively form a portion of the fluid flow pathway 12 for performing at least one step of the chemical reaction. Alternatively, each flow connector 26 can be configured to selectively be disengaged from flow connectors forming the fluid flow pathway such that the flow connector is not in fluid communication with the fluid flow pathway. In exemplary aspects, each flow connector 26 can have opposing inlet/outlet openings 28 that can function as an inlet or an outlet depending upon the direction of fluid flow in a particular flow pathway configuration. As depicted in FIG. 16, it is contemplated that the flow connectors 26 can be positioned within a channel 23 extending along the length of the substrate 22. In further aspects, it is contemplated that the outer surface 24 of the substrate 22 can define connection openings 25 that are configured to permit fastening of a surface-mounted component (e.g., module) to the substrate. It is further contemplated that the inlet/outlet openings 28 of the flow connectors 26 can project upwardly or downwardly from adjoining portions of the flow connector to engage the inlets or outlets of modules or other flow connectors as disclosed herein.

In exemplary aspects, it is contemplated that each module 50 of the plurality of modules can have a common base structure that includes a plurality of openings that are configured to receive fasteners (e.g., bolts or screws) for mounting the module to the outer surface 24 of the substrate 22. In these aspects, it is contemplated that the locations of the openings within the base structure of each module 50 can be complementary to corresponding connection openings 25 defined within the substrate layer 20. It is further contemplated that the common base structure can include a common dimensional profile, such as, for example and without limitation, a square profile, which can optionally include length and width dimensions of about 1.5 inches. In some exemplary aspects, the disclosed modules 50 can be directly mounted to a substrate 22 as disclosed herein. Alternatively, in other exemplary aspects, and as shown in FIG. 16, the disclosed modules 50 can be mounted to a base plate 55 that is in turn mounted to a substrate 22 as disclosed herein.

Figure 14:
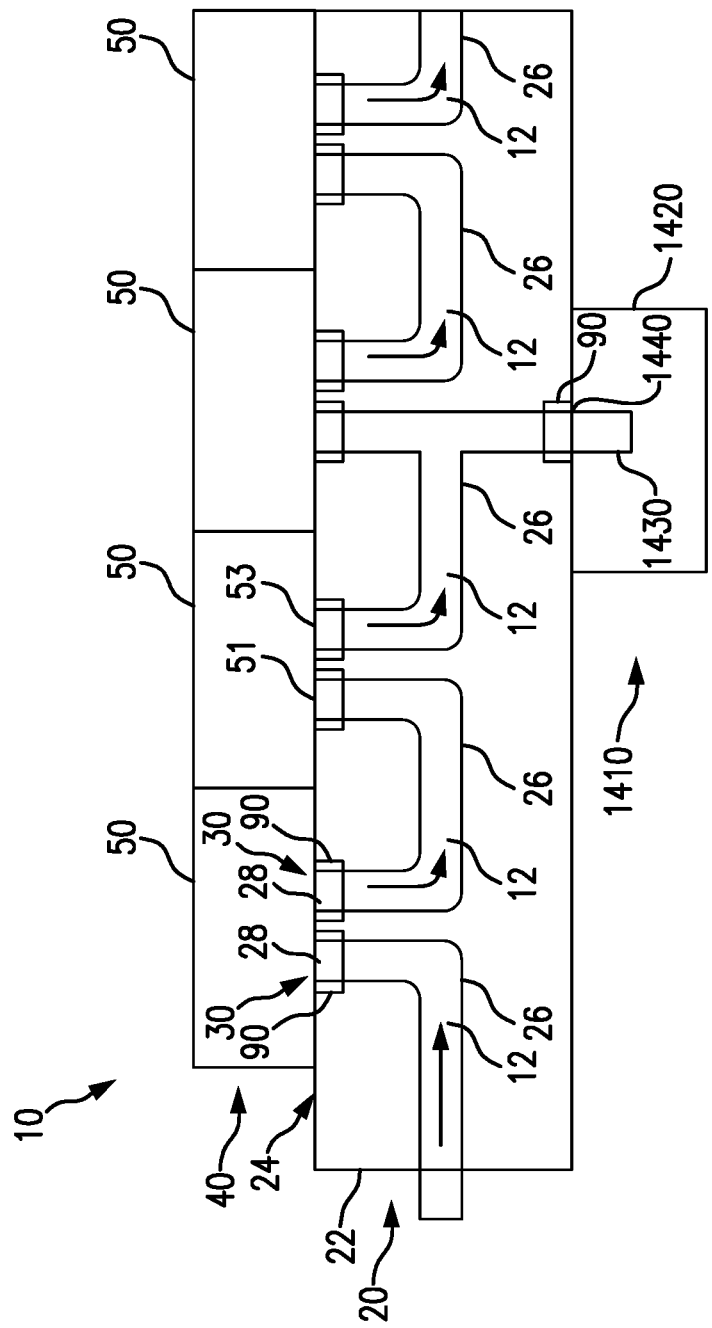
FIG. 14 is a schematic diagram (side view of the system) of a portion of an exemplary reaction system having a manifold layer.
Figure 15:
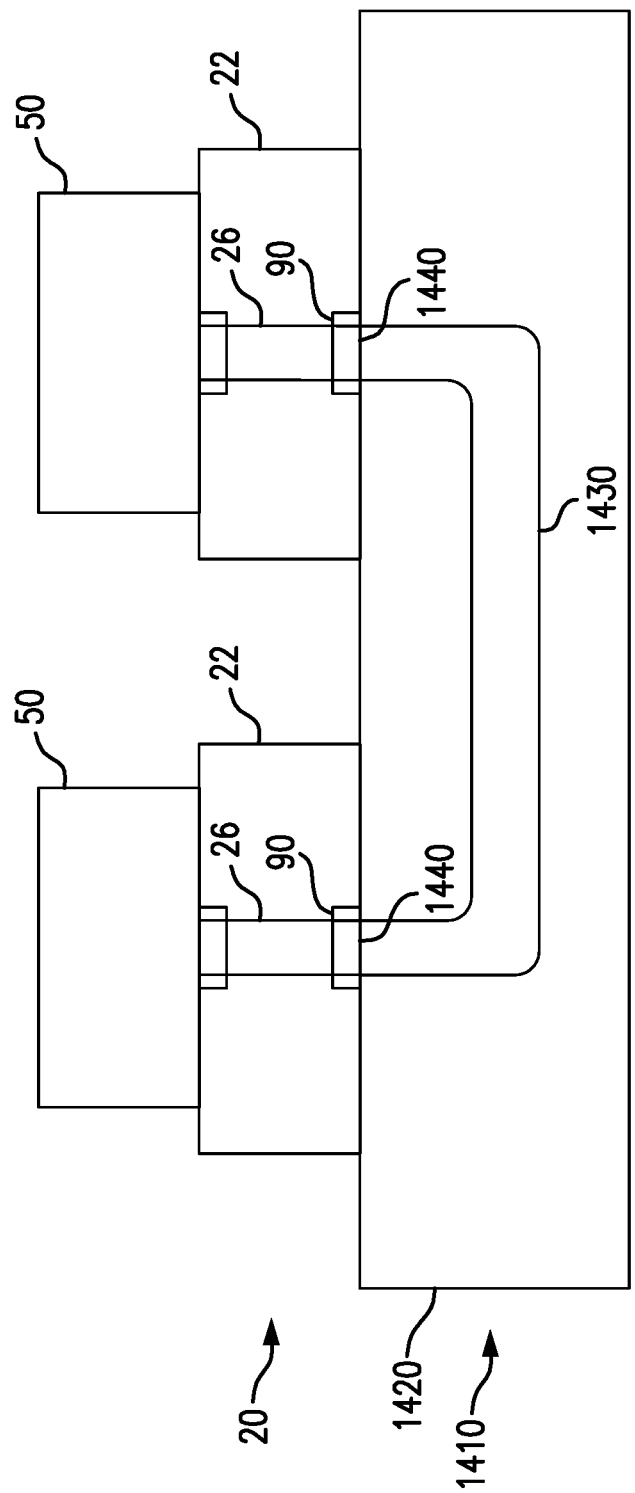
FIG. 15 is a schematic diagram (end view of the system) of a portion of an exemplary reaction system having a manifold layer.

Optionally, in further aspects, and as shown in FIG. 14-FIG. 16, the modular chemical reaction system 10 can further comprise a manifold layer 1410. In these aspects, the manifold layer 1410 can comprise at least one manifold body 1420 underlying the substrate layer 20. Optionally, the manifold body 1420 can comprise a plurality of manifold bodies that are selectively positioned in parallel to establish a framework for parallel fluid passageways as disclosed herein. Alternatively, it is contemplated that the manifold body 1420 can be a single contiguous platform structure. In use, it is contemplated that the manifold bodies 1420 can be oriented perpendicular to the substrates 22 disclosed herein in order to provide for conveyance of reaction components among parallel substrates. Alternatively, in other aspects, a manifold body 1420 can be oriented parallel to (or directly underlie) a substrate body to permit bypassing of certain reaction modules aligned with a particular substrate body. In exemplary aspects, it is contemplated that the plurality of flow connectors 26 of the system can comprise a first plurality of flow connectors 26 positioned within the substrate layer 20 and a second plurality of flow connectors 1430 positioned within the manifold layer 1410. Each flow connector 1430 of the manifold layer 1410 can have opposing inlet/outlet openings 1440 that can function as an inlet or an outlet depending upon the direction of fluid flow in a particular flow pathway configuration. As depicted in FIG. 16, it is contemplated that the flow connectors 1430 can be positioned within a channel 1630 extending along the length of the manifold body 1420. In further aspects, it is contemplated that the manifold body 1420 can have an outer surface 1610 that defines connection openings 1620 that are configured to permit fastening of a substrate 22 to the manifold body. It is further contemplated that the inlet/outlet openings 1440 of the flow connectors 1430 can project upwardly or downwardly from adjoining portions of the flow connector to engage the inlets or outlets of modules or other flow connectors as disclosed herein.

It is contemplated that the disclosed flow connectors 26, 1430 of the substrate layer and the manifold layer can be provided in a range of varying lengths and shapes to permit connection with other flow connectors and a variety of modules as disclosed herein.

Although depicted in FIG. 14-FIG. 16 as having two layers (the substrate layer 20 and the manifold layer 1410) beneath the surface-mount layer 40, it is contemplated that the disclosed system can have additional layers below the manifold layer 1410 to permit further fluid pathway modification.

Figure 17:
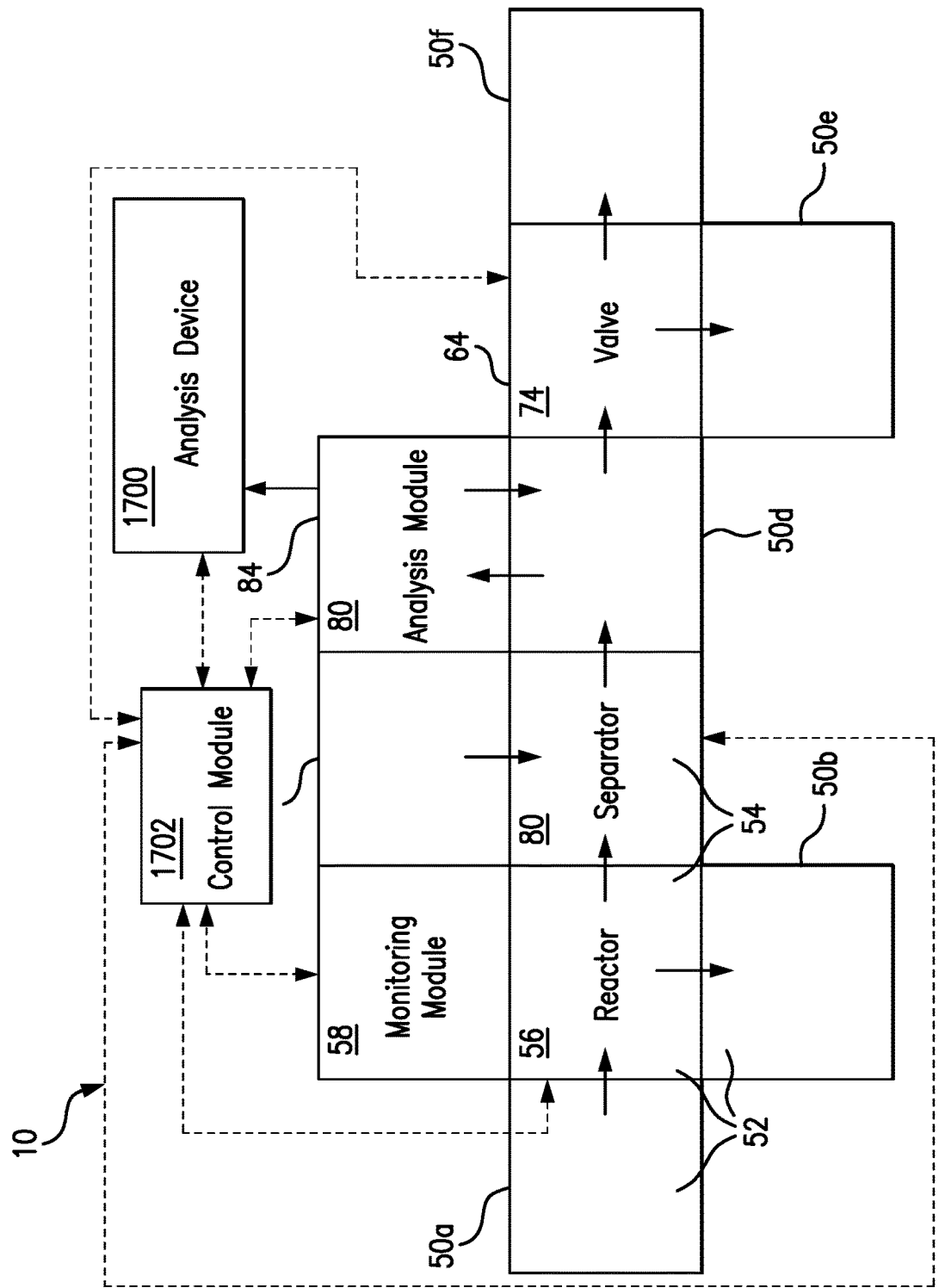
FIG. 17 is a schematic diagram providing a top view of an exemplary reaction system having surface-mounted process modules (reactors, separators), regulator modules (temperature modules, valves, pressure sensor modules), and analysis modules (for connection to an analysis device) as disclosed herein.
Figure 18:
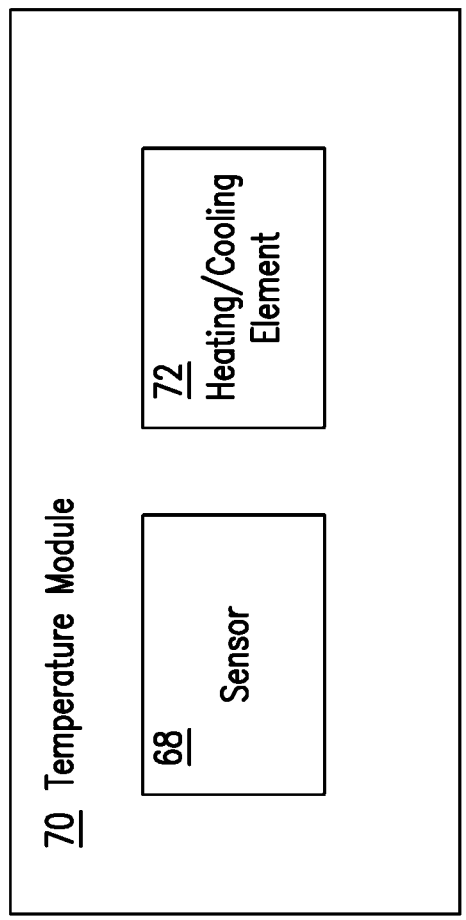
FIG. 18 is a schematic view of an exemplary temperature module having a temperature sensor and a heating/cooling element.

In additional aspects, and with reference to FIG. 17-FIG. 18, the plurality of modules 50 can comprise at least one monitoring module 58 that is configured to produce at least one output indicative of at least one condition of a chemical reaction. In these aspects, it is contemplated that the at least one monitoring module 58 (optionally, a plurality of monitoring modules) can be communicatively coupled to processing circuitry as further disclosed herein. Exemplary conditions that can be monitored by the at least one monitoring module 58 include, but are not limited to temperature, pressure, flow rate, an identification of products generated by a reaction, a rate of consumption of a reagent, an identification of side products, yield, selectivity, purity, and the like. It is contemplated that the at least one monitoring module can comprise sufficient sensors, hardware, or processing components that are capable of generating outputs corresponding to the conditions monitored by the at least one monitoring module 58.

In further exemplary aspects, at least one flow module 52 of the plurality of flow modules can be a process module 54 that can correspond to a location of a step of the chemical reaction. Optionally, each process module 54 disclosed herein can also serve as a monitoring module 58, where the process module 54 is also configured to provide at least one output to processing circuitry as further disclosed herein. Examples of such process modules 54 include a reactor 56 or a separator 60 as further disclosed herein. In one aspect, when the at least one process module 52 comprises a reactor 56, it is contemplated that the reactor can be a heated tube reactor, a packed-bed reactor, or combinations thereof. However, it is contemplated that other reactors can be used, provided they have the surface-mount capabilities disclosed herein. In another aspect, when the at least one process module 52 comprises a separator 60, the separator can be a liquid/liquid separator or a gas/liquid separator. In one optional aspect, the separator 60 can comprise a membrane-based liquid-liquid separator as further disclosed in the Examples section of this application. In another optional aspect, the separator 60 can comprise a gravity-based liquid-liquid separator as further disclosed in the Examples section of this application. In this aspect, and as further described herein, it is contemplated that the gravity-based liquid-liquid separator can be configured for use under pressures above atmospheric conditions as is conventional. It is further contemplated that the disclosed gravity-based liquid-liquid separator can comprise glass that permits visibility of the separation process. It is still further contemplated that the disclosed gravity-based liquid-liquid separator can provide inlet and outlet flow paths that travel in a common plane rather than in different planes as is conventional. In further aspects, it is contemplated that the separator 60 can comprise a gravity-based gas-liquid separator as further disclosed in the Examples section of this application.

Optionally, in exemplary configurations, the plurality of flow modules 52 of the system can comprise at least one reactor 56 and at least one separator 60.

Optionally, in exemplary aspects, it is contemplated that each flow connector 26 of the substrate layer 20 (and each flow connector 1430 of the manifold layer 1410, when present) can have a consistent inner diameter along its entire length (optionally, ranging from about 0.04 inches to about 0.08 inches). Optionally, in these aspects, the at least one flow module 52 of the system 10 can comprise a reactor 56 and/or separator 60, and at least one of the fluid inlet 51 and the fluid outlet 53 of the at least one flow module 52 can share a consistent inner diameter with an adjacent flow connector 26 of the plurality of flow connectors. Optionally, in still further exemplary aspects, at least a portion of the flow connectors 26, 1430 (optionally, each flow connector) of the plurality of flow connectors can comprise Hastelloy C276. In contrast to known flow connectors, which have a variable inner diameter at various locations, it is contemplated that the disclosed flow connectors can provide improved performance by minimizing dead space and providing improved fluid flow (particularly in liquid reactions).

Optionally, in further exemplary aspects, the plurality of modules 50 of the modular chemical reaction system 10 can comprise at least one regulator module 64. Optionally, in these aspects, each regulator module 64 disclosed herein can also serve as a monitoring module 58, where the regulator module 64 is also configured to provide at least one output to processing circuitry as further disclosed herein. In exemplary aspects, it is contemplated that each regulator module 64 can be positioned in fluid or thermal communication with the fluid flow pathway 12 and configured to achieve, maintain, and/or measure one or more desired conditions of the chemical reaction. Optionally, the plurality of modules 50 of the system 10 can include at least one process module 54 and at least one regulator module 64. Exemplary regulator modules 64 include, for example and without limitation: a check valve, a tee filter, a flow regulator, a pressure sensing module, a pressure relief valve, a back pressure regulator, a tube adaptor, a valve, a pump, a flow stream selector, a control valve module, a temperature monitoring module, a temperature control module, a heater, a cooler, or combinations thereof. In exemplary aspects, it is contemplated that at least one regulator module 64 can comprise a sensor (e.g., a temperature, pressure, or flow sensor) positioned in fluid and/or thermal communication with a portion of the fluid flow pathway and configured to produce an output indicative of at least one characteristic of fluid (e.g., liquid) within the regulator module (in this case, a flow module as well). For example, as shown in FIG. 18, a temperature module 70 can comprise a temperature sensor 71 and, optionally, also comprise heating and/or cooling element 72 as is known in the art and further disclosed herein. In other exemplary aspects, it is contemplated that at least one regulator module 64 can be configured to effect adjustment of at least one property of the fluid within the fluid flow pathway. For example, a valve module 74 can be configured to move among at least first and second positions to modify flow of fluid through the fluid flow pathway. Optionally, it is contemplated that each valve module 74 can comprise a servo motor and position sensors (e.g., encoders) that are communicatively coupled to the processing circuitry as further disclosed herein to permit selective monitoring and/or control of valve positioning.

In exemplary aspects, it is contemplated that the system 10 can comprise at least one analysis device 1700. In these aspects, each analysis device 1700 can be positioned in operative communication with the fluid flow pathway 12 through at least one module 50. As used in this context, the term "operative communication" can refer to any form of communication necessary to permit analysis by an analysis device 1700 as disclosed herein. It is further contemplated that each analysis device 1700 can be configured to produce at least one output indicative of at least one characteristic of the chemical reaction as the chemical reaction occurs. In further aspects, each analysis device 1700 can comprise: a UV-Vis spectrometer, a near-infrared (NIR) spectrometer, a Raman spectrometer, a Fourier Transform-Infrared (FT-IR) spectrometer, a nuclear magnetic resonance (NMR) spectrometer, or a mass spectrometer (MS). More generally, it is contemplated that the analysis device 1700 can be any conventional Process Analytical Technologies (PAT) device that is suitable for use in at least one step of a chemical reaction or a series of chemical reactions. It is further contemplated that one or more analysis device can be placed along the flow path of the system 10, wherein each of the analysis devices can send output analyses to the processing circuitry for monitoring or further optimizing the one step of the chemical reaction or the series of chemical reactions being performed. In exemplary aspects, the plurality of modules 50 can comprise at least one analysis module 80 having at least a second outlet 84 that is positioned in operative communication with an analysis device 1700 as disclosed herein. Optionally, in these aspects, it is contemplated that the analysis module 80 can be positioned upstream of at least one other flow module of the plurality of flow modules. However, in other aspects, it is contemplated that the analysis module 80 can be positioned at a location corresponding to an end or completion of a reaction. In some exemplary aspects, it is contemplated that the analysis module 80 can be communicatively coupled to the analysis device 1700. In these aspects, it is contemplated that the analysis module 80 can serve as a monitoring module 58 as further disclosed herein.

In further exemplary aspects, the system 10 can comprise processing circuitry 110. In these aspects, it is contemplated that the processing circuitry 110 can be communicatively coupled to at least one module of the plurality of modules 50 (e.g., at least one monitoring module 58) and the at least one analysis device 1700. It is further contemplated that the processing circuitry 110 can be configured to receive the at least one output from the at least one module (e.g., monitoring module 58). Optionally, the processing circuitry 110 can receive a plurality of outputs from a plurality of modules (e.g., monitoring modules), either sequentially or simultaneously. Optionally, the processing circuitry 110 can use the at least one output to adjust operation of at least one module 50 (e.g., a process module 54 and/or a regulator module 64) to optimize the chemical reaction or a portion of the chemical reaction. Additionally, or alternatively, it is further contemplated that the processing circuitry 110 can be configured to receive the at least one output from the at least one analysis device 1700. Optionally, the processing circuitry 110 can receive a plurality of outputs from a plurality of analysis devices, either sequentially or simultaneously. Optionally, the processing circuitry 110 can use the at least one output to adjust operation of at least one module 50 (e.g., a process module 54 and/or a regulator module 64) to optimize the chemical reaction or a portion of the chemical reaction. In exemplary aspects, the processing circuitry can simultaneously or sequentially receive outputs from at least one module (e.g., monitoring module) and at least one analysis device as a reaction occurs.

In additional aspects, it is contemplated that the processing circuitry can respond to the outputs received from the monitoring module 58 and/or the analysis device 1700 to adjust specific reaction parameters based upon pre-set conditions saved within the processing circuitry (i.e., within a memory of the processing circuitry) or based upon adjustments made through user inputs (i.e., through user interfaces positioned in communication with the processing circuitry).

In some aspects, a user can manually trigger a change in any one of the modules by changing one or more parameters in the processing circuitry based upon outputs from one or more monitoring modules and/or one or more analysis devices as disclosed herein.

In some aspects, the disclosed processing circuitry (optionally, in the form of a controller) can be used to automatically orchestrate changes to one or more modules of the system based upon outputs from one or more monitoring modules and/or one or more analysis devices as disclosed herein, where changes are based upon a pre-set trigger (such as a pre-determined threshold temperature or yield parameter), which can optionally be stored in the memory of the processing circuitry. For example, if the temperature of a given reaction is beyond a pre-set threshold temperature, the processing circuitry can send instructions/commands to the corresponding temperature regulator to reduce the temperature for that reactor for that particular reaction until the temperature drops below the threshold temperature value.

An exemplary schematic flow diagram of a system 10 is provided in FIG. 17. Each contiguous box corresponds to a respective module 50; although shown contiguously, it is understood that the modules need not be in direct contact with one another. The solid arrows within the contiguous boxes represent flow of fluid within a fluid pathway as disclosed herein, while the dashed arrows represent communication among system components. Module 50a receives an inlet feed of fluid, and an underlying flow connector delivers the fluid to the adjacent separator module 60. Separator module 60 is shown in thermal communication with monitoring module 58 and in fluid communication with reactor 56 and module 50b, each of which receives a different separation product. The monitoring module 58 can monitor one or more conditions during the separation step. Optionally, in one example, the monitoring module 58 can be a temperature module 70 that can be configured to monitor temperature during the separation step and optionally be configured to provide additional heat or cooling to maintain a desired or selected temperature as disclosed herein. Module 50c represents another inlet feed source that delivers additional fluid into reactor 56. The products of the reaction within reactor 56 are delivered to module 50d, which is in fluid communication with analysis module 80, which is in turn in operative communication with an analysis device 1700 as disclosed herein. Module 50d is also in fluid communication with valve 74, which can be selectively adjusted to direct fluid toward either module 50e or module 50f. As further disclosed herein, it is contemplated that at least a portion of the disclosed modules can be communicatively coupled to the processing circuitry 110, which can be used to provide active feedback and/or modification to the surface-mounted system components.

Figure 19:
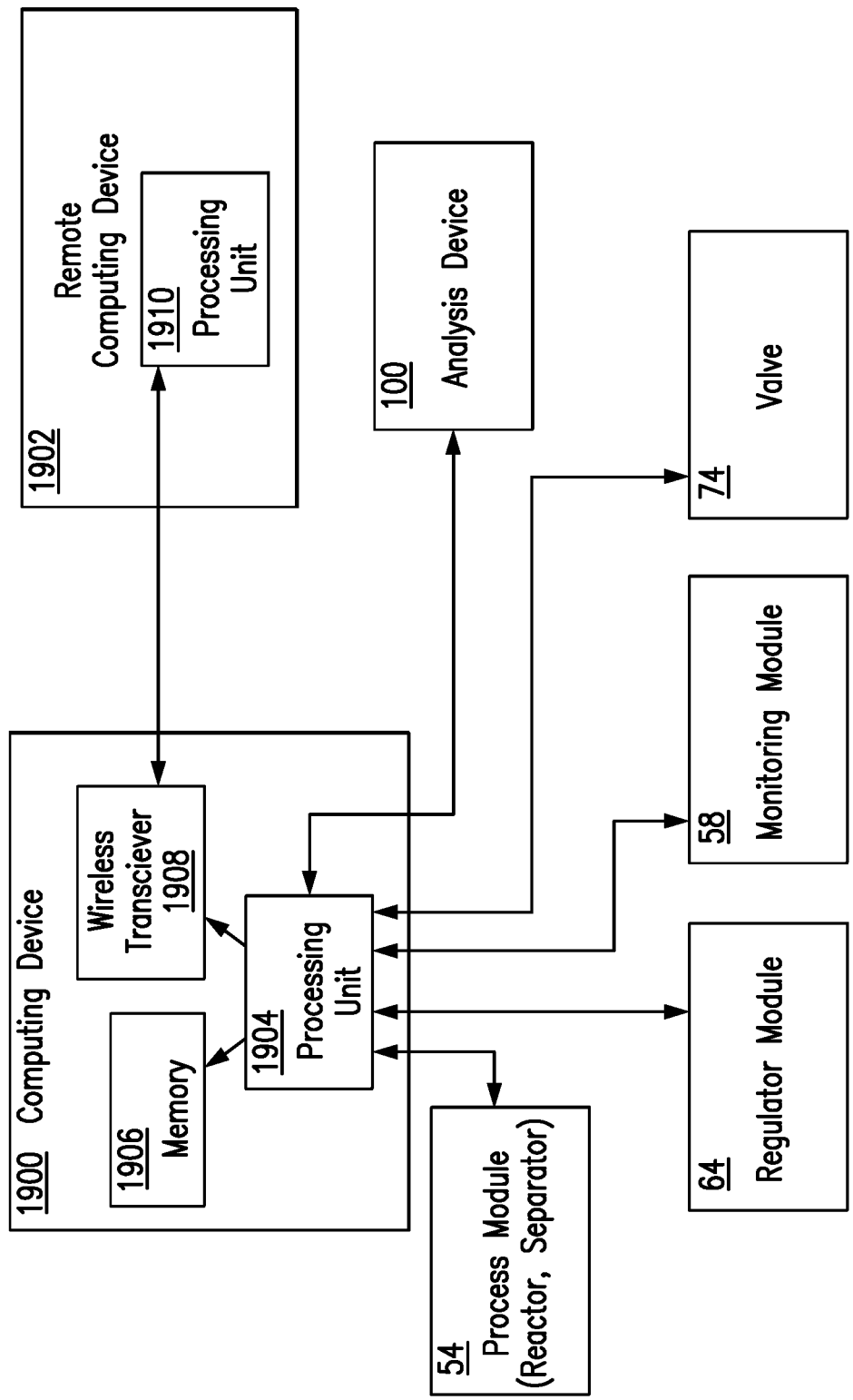
FIG. 19 is a schematic diagram depicting communication between a computing device and various components of a modular reactor system as disclosed herein.

FIG. 19 depicts an exemplary configuration in which the surface-mounted components of the system can be communicatively coupled to processing circuitry, such as a computing device 1900 (optionally, a plurality of computing devices) as further disclosed herein. Non-limiting examples of the computing device 1900 include a desktop computer, a laptop computer, a central server, a mainframe computer, a tablet, a smartphone, and the like. In exemplary aspects, the computing device 1900 can be positioned in the vicinity of the system 10. For example, in various exemplary aspects, and as shown in FIG. 17, it is contemplated that at least one computing device 1900 of the system can be a control module 1702, which can be selectively surface-mounted as disclosed herein or otherwise positioned in the vicinity of the surface-mounted components. In these aspects, it is contemplated that a plurality of control modules 1702 can be selectively positioned within the system 10 to form desired feedback loops as disclosed herein. The computing device 1900 can be configured to generate, receive, store, and/or transmit equipment data related to the modular chemical reaction system. For example, the computing device 1900 may receive such equipment data from one or more of the process module 54, the regulator module 64, the monitoring module 58, the valve 74, and/or the analysis device 1700. The computing device 1900 may provide such equipment data to the route engine 140 and/or to a computing device associated with the route engine 140. The computing device 1900 may be further configured to receive one or more synthetic routes from the route engine 140 and cause the execution of the one or more synthetic routes on the modular chemical reaction system.

As shown in FIG. 19, it is contemplated that the computing device 1900 can comprise a processing unit 1904 (e.g., a CPU) that is in communication with a memory 1906. In exemplary aspects, the processing unit 1904 can be communicatively coupled to at least one module 50 of the system 10 using conventional wired (e.g., cable, USB) or wireless (WiFi, Bluetooth) communication protocols. Additionally, or alternatively, it is contemplated that the processing unit 1904 can be communicatively coupled to at least one analysis device 1700 using conventional wired (e.g., cable, USB) or wireless (WiFi, Bluetooth) communication protocols. It is contemplated that the processing unit 1904 can be communicatively coupled to at least one monitoring module 58 (e.g., a plurality of monitoring modules) as further disclosed herein. In exemplary aspects, the processing unit 1904 can be communicatively coupled to at least one process module 54. Additionally, or alternatively, in further exemplary aspects, the processing unit 1904 can be communicatively coupled to at least one regulator module 64, such as a temperature module 70 or a valve 74.

Optionally, the computing device 1900 can comprise a wireless transceiver 1908 (e.g., a WiFi or Bluetooth radio) that is configured to wirelessly transmit and receive information. In exemplary aspects, it is contemplated that the wireless transceiver 1908 can be communicatively coupled to a remote computing device 1902, such as a tablet, a smartphone, or other computing device positioned at a location remote from the system. In these aspects, the remote computing device 1902 can be configured to provide remote user inputs or monitor progress of an ongoing reaction based upon outputs received from the computing device 1900 (optionally, through WiFi, a cellular network, or a Cloud-based system). The remote computing device may comprise a processing unit 1910.

FIG. 17 also includes an exemplary schematic communication diagram of the system 10. As shown, it is contemplated that a plurality modules of the system can be communicatively coupled to processing circuitry, shown here as a control module 1702. During performance of at least one step of a reaction using the disclosed system, it is contemplated that one or more monitoring modules 58 and one or more analysis devices 100 can be configured to provide outputs to the processing circuitry as further disclosed herein. In the depicted example, monitoring module 58, reactor module 56, separator 60, analysis module 80, valve module 74, and the analysis device 1700 are all communicatively coupled to control module 1702, thereby allowing for direct monitoring of various reaction conditions and characteristics as the reaction occurs. However, in other exemplary configuration, as few as one module may be in communication with the processing circuitry. Optionally, it is further contemplated that the control module 1702 (alone or in combination with other processing circuitry or a remote computing device as disclosed herein) can be configured to selectively adjust operation of at least one module (e.g., a process module (reactor 56, separator 60) or a regulator module (valve 74)) to optimize the chemical reaction. Exemplary characteristics and conditions that can be optimized using the disclosed feedback loops include, for example and without limitation, one or more of pressure, temperature, an identification of generated products, reagent consumption rate, identification of side products, product yield, selectivity, and purity.

In exemplary aspects, at least a portion of the plurality of modules can cooperate with at least a portion of the plurality of flow components to produce a first configuration that forms a first fluid flow pathway for performing at least one step of a first chemical reaction. After completion of the first chemical reaction, the plurality of modules and the flow components within the substrate layer can be configured for selective rearrangement to a second configuration within a minimal changeover period to produce a second fluid flow pathway for performing at least one step of a second chemical reaction. In these aspects, it is contemplated that the second configuration of modules and flow components can include at least one module that did not define a portion of the first fluid flow pathway. It is further contemplated that the modules and flow components that define the second fluid flow pathway can comprise at least a portion of the modules and flow components that defined the first fluid flow pathway. It is still further contemplated that the number of modules included in the second fluid flow pathway can be less than, equal to, or greater than the number of modules included in the first fluid flow pathway. Optionally, in exemplary aspects, the locations of the plurality of modules and the plurality of flow connectors with respect to the substrate (and manifold layers) can remain unchanged in the first and second fluid flow pathways. In these aspects, it is contemplated that the first fluid flow pathway can be modified by changing flow positions within valves (but not adjusting the mounted position of the valve module with respect to the substrate) to thereby adjust the flow pathway. Optionally, such modifications can allow for bypassing portions of the first fluid pathway (e.g., process modules) and/or directing fluid to other modules (e.g., process modules) that were previously not in fluid communication with the first fluid flow pathway. Although not required, in some optional aspects, it is contemplated that modules can be removed, added, or replaced to selectively adjust the fluid flow pathway. Thus, in some exemplary aspects, the modified second fluid flow pathway can be produced by adjusting fluid flow within a valve module and removing, adding, or replacing at least one module of the system. With the addition or removal of modules as disclosed herein, it is contemplated that the position and/or number and/or type of flow connectors can be adjusted to accommodate the change in the fluid flow pathway.

In further exemplary aspects, it is contemplated that the minimal changeover period can permit sequential performance of multiple chemical reactions in a limited time window that is far smaller than possible with conventional reaction structures. Optionally, the minimal changeover period can range from about 30 minutes to about 4 hours or, more typically, from about 1 hour to about 2 hours, depending upon the complexity of the reaction.

Optionally, the disclosed system 10 can comprise a plurality of regulator modules 64. In exemplary aspects, it is contemplated that the first and second configurations of the plurality of modules and the plurality of flow components can comprise respective first and second arrangements of regulator modules, with the first and second arrangements of regulator modules differing from one another with respect to at least one of module positioning and type of modules. Optionally, in some exemplary aspects, it is contemplated that each arrangement of regulator modules can comprise at least five of the following: a check valve, a tee filter, a flow regulator, a pressure sensing module, a pressure relief valve, a pressure regulator, a tube adaptor, a valve, a pump, a control valve module, a temperature monitoring module, a temperature control module, a heater, or a cooler. Optionally, in these aspects, the second configuration can include at least one module type that is not present in the first configuration. It is further contemplated that the second configuration can include more or fewer regulator modules than were included in the first configuration.

In further exemplary aspects, it is contemplated that the disclosed system can permit performance of multiple or separate reaction steps simultaneously. For example, in one exemplary application, separate products or byproducts from a process module (e.g., a separator module after a separation step) can be delivered to distinct modules (and separate downstream flow paths) for further analysis and/or processing (reaction, separation) as disclosed herein.

Optionally, the disclosed system 10 can comprise a plurality of analysis devices. In exemplary aspects, it is contemplated that a first configuration of the plurality of analysis devices can be in operative communication with the first fluid flow pathway, and the plurality of modules and the flow components within the substrate layer can be configured for selective rearrangement to establish operative communication between a second configuration of the plurality of analysis devices and the second fluid flow pathway. In these aspects, it is contemplated that the first and second configurations of the plurality of analysis devices can include at least two of the following: a UV-Vis spectrometer, a near-infrared (NIR) spectrometer, a Raman spectrometer, a Fourier Transform-Infrared (FT-IR) spectrometer, a nuclear magnetic resonance (NMR) spectrometer, or a mass spectrometer (MS). Optionally, in these aspects, the second configuration of the analysis devices can include at least one analysis device type that is not present in the first configuration. It is further contemplated that the second configuration can include more or fewer analysis devices than were included in the first configuration.

An exemplary method of using the disclosed systems can comprise introducing at least one reagent (e.g., liquid reagent) into the fluid flow pathway of the system and then performing a chemical reaction using the at least one reagent (e.g., liquid reagent).

Optionally, in some aspects, the at least one process module comprises a plurality of process modules, and the chemical reaction can be a multi-step chemical synthesis comprising a plurality of sequential steps. In these aspects, it is contemplated that each step of the plurality of sequential steps can correspond to flow of reagents within a respective process module.

In further aspects, the method can comprise modifying the fluid flow pathway to produce a second fluid flow pathway different than the first fluid flow pathway as disclosed herein. As further described herein, the second fluid flow pathway can be different from the first fluid flow pathway in: number of flow modules, number of monitoring modules, location of monitoring modules, number of process modules, type of process modules, sequence of process modules, location of process modules, number of regulator modules, type of regulator modules, location of regulator modules, number of analysis modules, location of analysis modules, direction of flow, and combinations thereof. Further, the method can comprise running a second chemical reaction using a modified fluid flow pathway including the additional process module.

Optionally, the modification of the first fluid flow pathway can comprise adjusting the flow of liquid through at least one valve module among the plurality of modules without the need for adjusting the position of any module relative to the substrate layer (or manifold layer). Optionally, it is contemplated that the fluid (e.g., liquid) flow path of the chemical reaction can be adjusted using valves without the need for adjusting the positions of the surface-mounted components and/or the positions and orientation of flow connectors as disclosed herein. Additionally, or alternatively, in other aspects, the modification of the first fluid flow pathway can comprise mounting an additional process module to the outer surface of the substrate. In these aspects, it is contemplated that the additional process module can be a reactor or a separator as disclosed herein. The method can further comprise establishing fluid communication between the additional process module and the fluid flow pathway.

In further aspects, the method can comprise using the processing circuitry as disclosed herein to receive at least one output from the at least one analysis device. In these aspects, the method can further comprise using the process circuitry to adjust operation of at least one module, such as a process module or a regulator module, to optimize the chemical reaction. Additionally, or alternatively, the method can comprise using the processing circuitry to receive at least one output from a monitoring module as disclosed herein (e.g., a process module or a regulator module equipped with a sensor). The method can further comprise using the processing circuitry to adjust operation of at least one module based upon the received at least one output to optimize the chemical reaction. Optionally, the monitoring and optimization of the chemical reaction can occur at locations within the system corresponding to intermediate steps in the chemical reaction. It is further contemplated that monitoring and optimization of the chemical reaction can take place as the reaction occurs.

As further disclosed herein, it is contemplated that monitoring modules and analysis modules can be selectively positioned at various positions along a reaction flow pathway depending upon the particular reaction steps/locations and conditions/characteristics that a user wishes to monitor.

In further exemplary aspects, it is contemplated that the disclosed system can function as a fully integrated platform for running and modifying chemical reactions. Optionally, each of the modules of the system can be communicatively coupled to the computing device 1900, which can be used to monitor and adjust each of the modules within the system based on feedback from analysis tools, including software executed by the processing unit 1904. In exemplary aspects, and as further disclosed herein, the system 10 can comprise a user interface for entering instructions for configuring a chemical reaction, and the processing unit can be configured to determine the appropriate modifications to achieve the selected configuration and to then effect automated modification of the plurality of modules as required to achieve the selected configuration.

In use, it is contemplated that the disclosed systems can allow for performing multi-step chemical synthesis reactions in a continuous manner not previously achievable. It is further contemplated that the disclosed systems can permit performance of modular liquid flow reactions that are not achievable using other surface-mount reactor systems. It is still further contemplated that the disclosed systems can provide for intermediate processing steps (at an intermediate step in a reaction) in a manner not previously achievable; previously, such processing could only be performed at the end of a reaction sequence. Additionally, it is contemplated that the disclosed systems can provide for reactions using smaller volumes of reagents, shorter residence times, and/or shorter heating times in comparison to previous chemical reactions.

In another aspect, disclosed herein are also integrated methods of using the above described restrosynthetic methods for discovery of potentially new synthetic routes along with a system able to quickly and cheaply screen and optimize such chemical reactions. An example apparatus includes a plurality of reaction vessels, a dispensing subsystem, at least one reactor module, an analysis subsystem, an automation subsystem, and control circuitry. The dispensing subsystem delivers reagents to the plurality of reaction vessels for a plurality of reaction mixtures having varied reaction conditions. The at least one reactor module drives a plurality of reactions within the plurality of reaction vessels. The analysis subsystem analyzes compositions contained in the plurality of reaction vessels. The automation subsystem selectively moves the plurality of reaction vessels from a location proximal to the dispensing subsystem to the at least one reactor module based on experimental design parameters. And, the control circuitry identifies optimum reaction conditions for a target end product based on the analysis. The full disclosure of this apparatus can be found in PCT/US2018/040421, filed on Jun. 29, 2018, entitled, "Apparatus for reaction screening and optimization, and methods thereof", the contents of which are incorporated by reference here in its entirety.

In various specific embodiments, an apparatus includes a plurality of reaction vessels, a dispensing subsystem, at least one reactor module, an automation subsystem, and control circuitry. The reaction vessels can be provided or contained within a substrate. The dispensing subsystem delivers reagents to the plurality of reaction vessels for a plurality of reaction mixtures having varied reaction conditions. The at least one reactor module drives a plurality of reactions within the plurality of reaction vessels and in accordance with the varied reaction conditions. For example, the at least one reactor module includes an energy emitter that provides an energy output toward the plurality of reaction vessels and thereby drive the plurality of reactions. The varied reaction conditions can include temperature, times, concentrations of reagents, reagents, among other variations. The analysis subsystem analyzes compositions of reaction mixtures (e.g., reactants, side products, end products, and byproducts) contained in the plurality of reaction vessels after the reactions have begun and, optionally, at any time during a set of reaction times. The analysis can be performed at a speed on an order of and/or up to one reaction per second (or more). The automation subsystem selectively moves the plurality of reaction vessels from a location proximal to the dispensing subsystem to the at least one reactor module based on experimental design parameters (e.g., that define the varied reaction conditions). The control circuit provides the experimental design parameters to the dispensing subsystem and the automation subsystem for feedback control of the plurality of reactions within a threshold period of time and to identify optimum reaction conditions for a target end product based on the analysis of the compositions received from the analysis subsystem.

In more specific embodiments, the feedback control provided by the control circuit adjusting the varied reaction conditions for a plurality of additional reactions based upon comparing previous reaction results with optimal reaction product yields stored in the analysis subsystem. For example, the control circuit provides the adjusted varied reaction conditions as revised experimental design parameters to the dispensing subsystem and the automation subsystem, which can be instantaneous or near-instantaneous.

The plurality of reaction mixtures can be exposed to the same or different additional reaction conditions (e.g., the same temperature, same exposure time, or various combinations of temperatures and/or exposure times). As a specific example, the varied reaction conditions can include exposure to different temperatures for different periods of time. The at least one reactor module can include a plurality of reactor modules or one reaction module with different zones that drive the plurality of reactions in parallel and at a plurality of different temperatures, and each of the reactor modules includes a thermal energy emitter that provides thermal energy toward at least a portion of the plurality of reaction mixtures. In such example embodiments, the reaction vessels are independently selectable from one another, and the automation subsystem selectively moves a first of the plurality of reaction vessels to a first location associated with the at least one reactor module, selectively moves a second of the plurality of reaction vessels to a second location associated with the at least one reactor module, and moves each of the first and second of the plurality of reaction vessels to a location proximal to the analysis subsystem upon completion of the respective reactions. In other embodiments, the reaction vessels or a subset can be located on a substrate and the substrate (as a whole) is moved to a reactor module and exposed to a temperature.

The automation subsystem can move the reaction vessels, reaction mixtures, substrates or other components (e.g., caps) to various locations associated with the apparatus. The reaction mixtures can be moved from a location proximal to the dispensing subsystem to the at least one reactor module for driving the reactions. The automation subsystem can additionally move the reaction mixtures (all or select ones) back to the dispensing subsystem for adding additional reagents and/or to the analysis subsystem. For example, the automation subsystem moves the reaction mixtures from the at least one reactor module to a location proximal to the analysis subsystem, and the analysis subsystem emits an analysis beam toward each of the plurality of reaction vessels that is approximately parallel to a top portion of the reaction vessels. In more specific embodiments, the control circuitry and the automation subsystem seal each of the plurality of reaction vessels prior to the plurality of reactions being driven within the reaction vessels, and unseal each of the plurality of reaction vessels mid-reaction to introduce other reagents to sample the reaction mixture, or prior to the analysis of the compositions of reaction mixtures (e.g., reactants, side products, end products, and byproducts).

Furthermore, the apparatus can optionally include one or more distribution chambers used for distributing the reaction vessels and the caps to the automation subsystem.

The dispensing system can include an inkjet printer, a liquid dispenser, and a combination thereof. For example, the inkjet printer can have a printer head, such as an 8-channel printer head, 9-channel printer head or 96-channel printer head, used to disperse the reagents to the reaction vessels.

The analysis subsystem can include a liquid chromatography-mass spectrometer (LC-MS), a real time (DART)-mass spectrometer (MS), a spectroscopic imager, and a combination thereof. For example, a component of the DART-MS provides a beam of gas directed toward each reaction mixture sequentially and carries a sampling of each reaction mixture to another component of the DART-MS. The beam can be provided toward the top of the reaction vessels, such as at an angle of 0-45 degrees relative to normal. The beam can result or cause a detectable audio frequency which can be used to verify analysis is being conducted. In some specific embodiments, the apparatus further includes sensor circuitry that provides a detectable audio frequency signal to the control circuitry in response to the analysis beam sampling of each reaction mixture, and the control circuitry compares the detected audio frequency signal to a threshold audio frequency and therefrom verifies whether analysis is occurring. In other embodiments, the apparatus can include imaging circuitry used to capture a visual image of the (e.g., each) reaction vessels and from the visual image, verifies whether analysis is occurring.

Other related and specific embodiments of the present disclosure are directed to an apparatus that includes a plurality of reaction vessels that are individually selectable and separable, at least one reactor module, an analysis subsystem, an automation subsystem, control circuitry. The plurality of reaction vessels includes reagents contained therein according to experimental design parameters for a plurality of reaction mixtures having varied reaction conditions. The at least one reactor module drives a plurality of reactions within the plurality of reaction vessels in accordance with the varied reaction conditions, the reaction varied conditions including exposure to different temperatures for different periods of time. The analysis subsystem analyzes compositions of reaction mixtures (e.g., reactants, side products, end products, and byproducts) contained within the plurality of reaction vessels after the reactions have begun and at any time during a set of reaction times by providing an analysis beam selectively toward the plurality of reaction mixtures and analyzing results therefrom at a speed on an order of one reaction per second, such as a speed of up to one reaction per second or more. The automation subsystem seals the plurality of reaction vessels, selectively moves the plurality of reaction vessels to and from the at least one reactor module for the different periods of time based on the experimental design parameters, and unseals the plurality of reaction vessels and selectively moves the reaction mixtures proximal to the analysis subsystem after reaction. The control circuitry provides the experimental design parameters to the automation subsystem for controlling the reactions within the plurality of reaction vessels and to identify optimum reaction conditions for a target end product based on the analysis of the compositions received from the analysis subsystem.

The automation circuitry, in specific aspects, includes a movable arm and a distribution chamber. The distribution chamber contains a plurality of caps for the plurality of reaction vessels. The movable arm and distribution chamber distribute the plurality of caps for the plurality of reaction vessels and seal the plurality of reaction vessels using the distributed caps. As further described herein, the movable arm can include head assembly used to select the reaction vessels and an interconnected set of links and power joints that can be used to move the head assembly.

In specific embodiments, the above-described apparatus can further include a dispensing subsystem that delivers reagents to the plurality of reaction vessels for the plurality of reaction mixtures having the varied reaction conditions. The automation subsystem can selectively move the plurality of reaction vessels from a location proximal to the dispensing subsystem to the at least one reactor module. And, the control circuitry provides the experimental design parameters to the dispensing subsystem, the experimental design parameters including identification of reagents, concentration of reagents for each of the plurality of reaction vessels, and the other varied reaction conditions.

Specific embodiments in accordance with the present disclosure are directed to a method of using the above-described apparatuses. The method can include providing a plurality of experimental design parameters, via control circuitry, to a dispensing subsystem and an automation subsystem for controlling a plurality of reactions within a plurality of reaction vessels. The method further includes delivering different amounts of reagents to respective reaction vessels of the plurality of reaction vessels by the dispensing subsystem and according to the experimental design parameters. The subsystem can selectively move the plurality of reaction vessels from a location proximal to the dispensing subsystem to the at least one reactor module, where the plurality of reactions are driven. For example, the plurality of reactions is driven within the plurality of reaction vessels in accordance with varied reaction conditions, including exposure to different temperatures and different periods of time, as defined by the experimental design parameters and by the at least one reactor module. The method further includes analyzing compositions contained within the plurality of reaction vessels at a speed on an order of (e.g., up to or more than) one reaction per second and identifying optimum reaction conditions for a target end product based on the analysis.

As described above, in some aspects, the method further includes selectively moving the plurality of reaction vessels to a location proximal to an analysis subsystem responsive to the plurality of reactions being driven to completion. The analysis subsystem provides a beam of gas that can be moveably directed toward each of the plurality of reaction vessels. The beam of gas can be directed at an angle that is approximately parallel to a top portion of the plurality of reaction vessels and the gas beam carries a sampling of the reaction mixture to an analysis subsystem for analyzing the compositions contained in the reaction vessels based on ions generated therefrom.

In various related aspects, the method includes delivering different amounts of reagents by providing a plurality of reaction mixtures having different concentrations of reagents to different reaction vessels of the plurality of reaction vessels according to the experimental design parameters. The reagents can be provided at the same time or at different times throughout the experiment.

Identifying the optimum reaction conditions for the target end product can further include identifying optimized experimental design parameters selected from the group consisting of: reagents, concentration of reagents, temperature, time, stoichiometry, and a combination thereof. The optimum reaction conditions can be further optimized by providing feedback. For example, the method can further include providing, based on the analysis of compositions contained within the reaction vessel, adjusted varied reaction conditions for a plurality of additional reactions designed to reach revised optimum reaction conditions for the target end product, and providing the adjusted varied reaction conditions as revised experimental design parameters to the dispensing subsystem and the automation subsystem. Using the revised experimental design parameters, the apparatus can run an additional test and further optimize the reaction conditions from an analysis of compositions therefrom.

Figure 20:
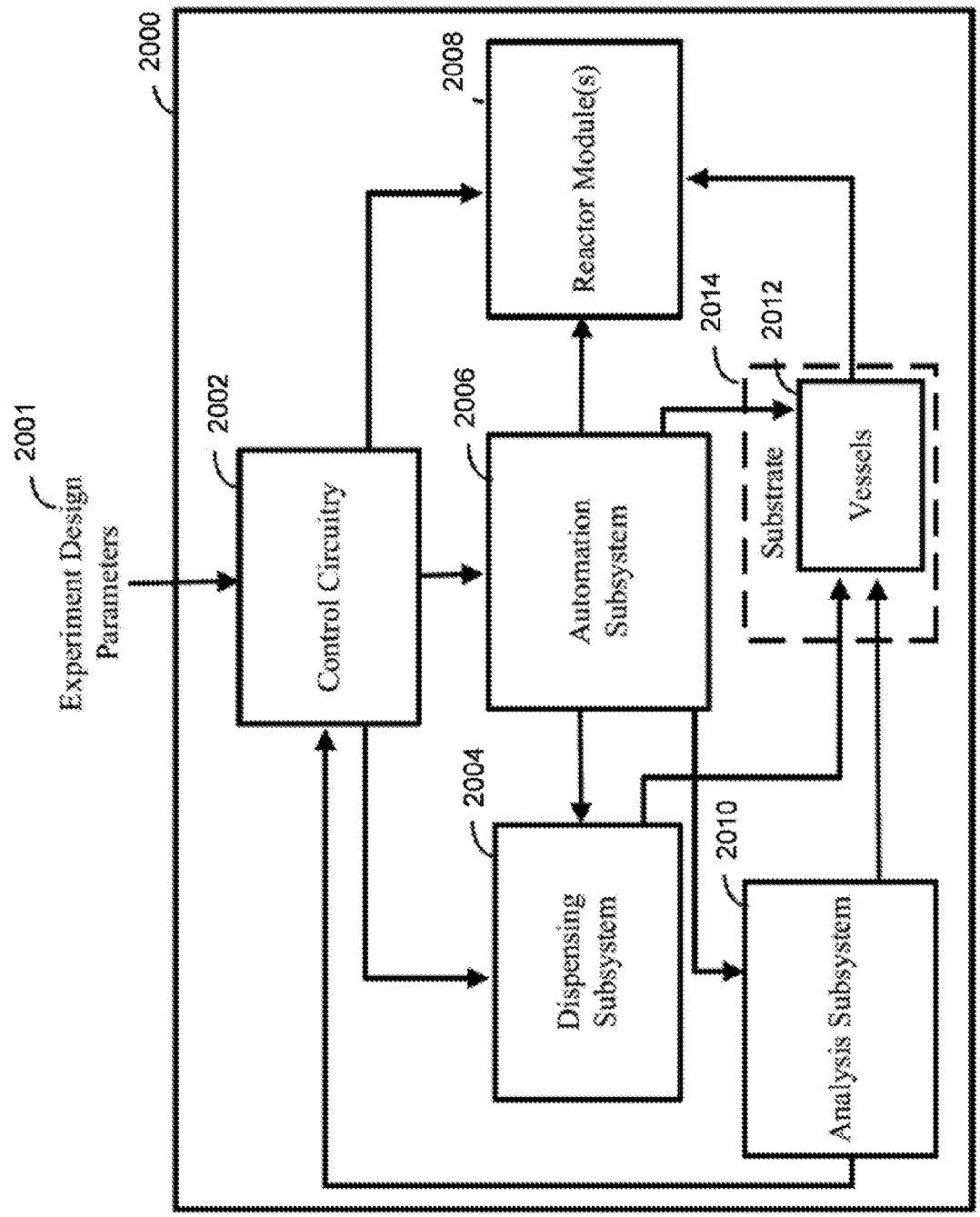
FIG. 20 illustrates an example of apparatus that performs reaction screening and optimization.

FIG. 20 illustrates an example of apparatus that performs reaction screening and optimization, in accordance with various embodiments. The apparatus 2000 includes a plurality of reaction vessels 2012, control circuitry 2002, a dispensing subsystem 2004, automation subsystem 2006, at least one reactor module 2008, and an analysis subsystem 2010. The apparatus 2000 can be used for synthetic design of target end products. More specifically, a plurality of synthetic routes having varied reaction conditions can be explored and used for screening or optimization of reaction conditions for reaching the target end product.

Different experimental design parameters 2001 can be input to control circuitry 2002 of the apparatus 2000 and used to explore a plurality of synthetic routes having the varied reaction conditions for reaching a target end product. The experimental design parameters 2001 may comprise one or more synthetic routes generated by the route engine 140. The experimental design parameters 2001 may comprise equipment data that is provided to the route engine 140 for consideration when generating synthetic routes. The experimental design parameters, which can also be referred to as DOE information, can include a plurality of sets of reactions conditions having different combinations of values. Example varied reaction conditions can include reagents, concentration of reagents or stoichiometry, when reagents are added, time, and temperature, among other conditions, and the values can include different actions or values of the conditions for the experiment (e.g., 50 degrees and 2000 degrees). Some DOE information in accordance with the present disclosure can eliminate the use of one-reaction condition-at-a-time optimization. For example, DOE information for four experimental design parameters (n<n>) can be reduced from 256 possibilities to thirty-two experiments or reaction mixtures. As may be appreciated, the DOE information can be designed and stored as data in a memory circuit of the control circuitry 2002.

The control circuitry 2002 receives the experimental design parameters 2001 and provides at least portions of the experimental design parameters (e.g., sets of reaction conditions) to other components of the apparatus 2000, such as to the dispensing subsystem 2004 and the automation subsystem 2006 and for controlling reactions based on the varied reaction conditions. For example, the experimental design parameters 2001 can define the varied reaction conditions, and can include a list of compounds and solvents, stoichiometry range, time and temperature conditions, and a normalized volume. The DOE information can include or be provided as a table that includes experiments to be run. In specific embodiments, a file can be generated by the control circuitry 2002 and sent to the dispensing subsystem 2004 for dispersing the reagents. For example, the control circuitry 2002 can provide combinations of reagents and at particular concentrations to the dispensing subsystem 2004 and can provide identification of a time for exposing the reaction mixtures (or a particular time for exposing each reaction mixture to a particular temperature or other type of energy used to drive the reaction) to the automation subsystem 2006. The automation subsystem 2006 can be provided with information about the at least one reactor module 2008, such as temperature(s) the one reactor module 2008 (or zones thereof) is configured to expose reaction mixtures to and/or which reactor module or zone to provide each reaction vessel to and/or for how long.

The plurality of reaction vessels 2012 are configured to contain reagents taking part in a reaction that is designed to generate a target end product. A variety of types of reaction vessels 2012 can be used, such as individual vials or wells. In some embodiments, the reaction vessels 2012 can be placed in or form part of a substrate 2014, such as a plate having the wells formed thereon and/or a plate having spaces (e.g., holes) of a size that the vials can be placed within. The substrate 2014 can take a variety of forms. For example, the substrate 2014 can include a tape that is flat and incorporates wells, an absorptive material to collect and mix the reagents, e.g., a Teflon or stainless steel mesh, or the plurality of vessels can formed as a well to contain the mixture. As another example, catalytic chemistry can be studied by using a palladium or other reactive metal mesh. In accordance with various embodiments, the reaction vessels 2012 are independently selectable from one another (e.g., vials), and can be selectively moved for different synthetic routes. In other embodiments, at least a subset of the reaction vessels 2012 are coupled together (e.g., wells on a plate) and are moved, together, for the synthetic routes.

The dispensing subsystem 2004, based on the varied conditions defined by the experimental design parameters 2001, delivers reagents to the plurality of reaction vessels 2012 for a plurality of reaction mixtures having the varied reaction conditions. More specifically, the plurality of reaction mixtures can include different amounts or concentrations of a set of reagents, and/or different reagents. Example dispensing subsystem 2004 include an Inkjet printer or a liquid dispenser. As further illustrated and described herein, the inkjet printer delivers reagents based on inkjet printing. An example inkjet printer can dispense volumes of pico liter to microliter volumes to a microliter plate using a multiple-channel print head, such as 9-channels, 12-channels, 96-channels. Each print head can contain a particular reagent. Inkjet printers can, for example, print reaction mixtures at a rate of one reaction per second. In addition, the reagents can be directly loaded into the apparatus 2000. For example, pre-weighted reagents loaded in matrix tubes can be input into the apparatus 2000. The pre-weighted reagents may be formatted in 96 tube tray holders that are barcoded for reagent location tracking and, optionally, sealed with inter slit-septum caps that can be directly mounted onto the print heads of the inkjet printer. Example dispensers include an inkjet printer and a print head.

However, embodiments are not limited to inkjet printers and can include a variety of different dispensing subsystems. For example, the dispensing subsystem can include a liquid dispenser that can be used to fill a plate and/or vials which are presented to the automation subsystem 2006 and/or manual dispenser (e.g., pipette).

The apparatus 2000 includes at least one reactor module 2008 having an energy emitter, such as a thermal energy tool or radiator, that provides an energy output (e.g., heat) toward the reaction mixtures for driving the plurality of reactions. Example energy emitters include a heater, an oven, a source of microwaves or light, etc. Each reactor module has at least one zone configured to provide a particular temperature or otherwise drive the reactions differently (e.g., provide different light or microwaves). For example, the at least one reactor module 2008 drives a plurality of reactions within the plurality of reaction vessels 2012 according to the varied reaction conditions. In a number of embodiments, the apparatus 2000 includes one reactor module that has one zone or is otherwise configured to provide a single temperature. Alternatively and/or in addition, the one reactor module can have a plurality of zones and/or the apparatus can include a plurality of reactor modules, each having one or more zones, and used to provide a plurality of different temperatures (e.g., two or more, six, ninety-six, etc). In such example embodiments, the at least one reactor module 2008 can drive a plurality of reactions within the reaction vessels 2012 by exposing the reaction mixtures to different temperatures and, optionally, for different periods of time. The different periods of time can be provided via the automation subsystem 2006 that moves one or more reaction vessels 2012 from the at least one reactor module 2008 at the end of the different periods of time. The different zones or different reactor modules can be used to drive the plurality of reactions in parallel and at a plurality of different temperatures (or other types of energy). As further illustrated and described herein, the reactor module can contain at a least a subset of reaction vessels 2012 which are provided to the reactor module by the automation subsystem 2006.

The automation subsystem 2006 can selectively move the reaction vessels 2012 and/or reaction mixtures within the reaction vessels 2012 based on the experimental design parameters 2001. More specifically, the automation subsystem 2006 moves the reaction vessels 2012 from a location proximal to the dispensing subsystem 2004 to the at least one reactor module 2008 for driving the reactions. As further illustrated herein, the automation subsystem 2006 can include a movable aim (e.g., a robot arm) and other movable components used to selectively move the reaction vessels 2012 and/or reaction mixtures. In some specific embodiments, the movement can include select movement of different reaction mixtures (e.g., vessels) to different reactor modules or zones and/or for different periods of time. In such a manner, the reaction mixtures as dispersed by the dispensing subsystem 2004 are moved to the at least one reactor module 2008 for driving the reactions therein, and, optionally, for different periods of time. The automation subsystem 2006 can further move the reaction mixtures to a location proximal to the analysis subsystem 2010 for analyzing compositions contained therein, although embodiments are not so limited, and the movement can occur using other mechanisms as further described herein. The compositions can include reactants, side products, end products, and byproducts, as well as various combinations thereof.

As a specific example, which is further described below, for reaction vessels that are individually selectable and an apparatus having multiple reactor modules or zones for providing a plurality of temperatures, the varied reaction conditions can include exposure to different temperatures for different periods of time. The automation subsystem 2006 selectively moves a first subset of the plurality reaction vessels to a first location associated with the at least one reactor module 2008 for exposing the first subset of vessels to a first temperature and moves a second subset of the reaction vessels to a second location of the at least one reactor module 2008 for exposing the second subset of vessels to a second temperature that is different than the first. Each of the reaction vessels in the first and second subsets are moved to a location proximal to the analysis subsystem 2010 upon completion of the respective reactions or as otherwise defined by the experimental design parameters 2001. The movement can be by the automation subsystem 2006 and/or an additional component, such as a conveyor belt as further described herein.

In accordance with a number of embodiments, the automation subsystem 2006 (based on control by the control circuitry 2002) can seal and/or unseal the reaction mixtures within the reaction vessels 2012. For example, each of the plurality of reaction vessels 2012 can be sealed prior to the plurality of reactions being driven within the reaction vessels 2012 by the automation subsystem 2006 and unsealed mid-reaction to introduce other reagents to sample the reaction mixture, or prior to the analysis of the compositions and based on the experimental design parameters 2001. For example, the automation subsystem 2006 can include the movable arm and a distribution chamber. The distribution chamber can contain a plurality of caps for the reaction vessels 2012. The movable arm, along with the distribution chamber, can distribute a cap to each of the plurality of reaction vessels 2012 and seal the reaction vessels using the caps. The movable arm can include or have access to a tool for subsequently unsealing the caps, as further illustrated herein.

The analysis subsystem 2010 analyzes compositions contained in the plurality of reaction vessels 2012 after the reactions have begun (and at any time during a set of reaction times defined by the experimental design parameters 2001). The compositions can be analyzed, for example, for a particular objective or set of objectives, such as product yield, selectivity, cost, purity, m/z values and various combinations. As an example, the end products are analyzed for yield, purity, and cost, and revised reaction conditions are generated to further optimize the one or more objectives. The analysis can be at a speed on an order of one reaction per second (e.g., up to one reaction per second or more and/or the range as previously described). Example analysis subsystem include a liquid chromatography-mass spectrometer (LC-MS), such as via a 96 well plate of via UV-plate readers (in which the plates do not include vials or include transparent vials), spectroscopic images (e.g., UV-Vis vials, FT-IR cells, etc.), and direct analysis in real time (DART)-mass spectrometer (MS) via individualized vials, and various combinations thereof. In various specific embodiments, the analysis subsystem 2010 includes a DART-source (e.g., a DART-MS) that provides a beam of gas directed toward each reaction mixture surface sequentially and carries a sample of each reaction mixture into the MS of the DART-MS. The analysis beam is an ionization source (e.g., beam of gas for DART-MS), in specific embodiments, and is emitted toward each of the plurality of reaction vessels in a manner that is approximately parallel (e.g., at an angle relative to normal) to a top portion of the reaction vessels 2012, although embodiments are not so limited. The beam of gas can be directed at an angle toward a top portion of the plurality of reaction vessels 2012 and the gas beam carries a sampling of the reaction mixture to another component of the analysis subsystem 2010 (e.g., the MS) that analyzes the compositions contained in the reaction vessels based on ions generated therefrom. The angle can include zero degrees with normal extending to the ceiling. In this manner, the reaction vessels 2012, such as with a liquid from 5-10 i and up to 20 ul (or the maximum volume of the vials), are opened and the DART head is directed across the vials directly into the MS. The beam can be directed at an angle of between 0-45 degrees to normal of the reaction vessels 2012.

In some embodiments, the angle of the beam of gas can generate a detectable audio frequency signal. In such example embodiments, the apparatus 2000 can optionally include sensor circuitry that outputs a signal in response to the detectable audio frequency signal to the control circuitry 2002. The sensor circuitry can provide a signal in response, which is used to verify that the analysis beam is sampling (or not) each reaction mixture. For example, the control circuitry 2002 can compare the detected audio frequency signal to a threshold audio signal (which indicates sampling) and therefrom verify whether analysis is occurring. In other embodiments, the apparatus 2000 can include imaging circuitry used to capture a visual image of the reaction vessels 2012 and from the visual image, verifies whether analysis is occurring.

In specific embodiments, the end products or other compositions can be compared to a target end product or target composition for an objective, such as selectivity and yield definitions for the target end product. The analysis subsystem 2010 provides the analysis of the compositions to the control circuitry 2002. The control circuitry 2002 identifies optimum reaction conditions (from among the varied reaction conditions) for a target end product based on the analysis of the compositions. More specifically, the optimum reaction conditions include a set of reaction conditions among the varied reaction condition for reaching a target end product, which may include reagents, concentration of reagents, temperature, time, stoichiometry, and a combination thereof. As previously described, the control circuitry 2002 can further provide feedback control of the plurality of reactions within a threshold time. The feedback control can include or be provided by adjusting the varied reaction conditions for a plurality of additional reactions based upon comparing previous reaction results with optimal reaction product yields stored in the analysis subsystem 2010 and providing the adjusted varied reaction conditions as revised experimental design parameters (e.g., a new plurality of sets of reaction conditions) to the dispensing subsystem 2004 and the automation subsystem 2006. The threshold period of time can include, in some specific embodiment, instantaneous or near-instantaneous control. The adjusted varied conditions can be for a plurality of additional reactions designed to reach revised optimum reaction conditions for the target end product and/or other target compositions (e.g., optimize one or more objectives). The control circuitry 2002 can provide the feedback control, e.g., the adjusted varied reaction conditions, as revised experimental design parameters to the dispensing subsystem 2004 and the automation subsystem 2006. The apparatus 2000 uses the revised experimental design parameters to run an additional test and further optimize reaction conditions from an analysis of the compositions therefrom.

The feedback control can provide the adjusted varied conditions using machine learning. For example, the control circuitry 2002 is trained with data, for molecular properties, such as the ability to inhibit an enzyme, act as an antimicrobial, catalyze a particular reaction, and predicting if a molecule has a relevant property. Over time, the control circuitry 2002 updates its training to predict what reaction conditions and/or values thereof impact particular objectives. The control circuitry 2002 is updated over time and uses this training to provide adjusted varied reaction conditions for one or more objectives and to further optimize the reaction conditions, as described above.

As a specific example, and which is consistent with the above-provided specific example, the plurality of reaction vessels 2012 include individual and separable reaction vessels. The automation subsystem 2006 places the reaction vessels 2012 into a substrate 2014 that is proximal to the dispensing subsystem 2004. The dispensing subsystem 2004 dispenses different amounts of reagents to respective reaction vessels of the plurality according to the experimental design parameters 2001. The plurality of reaction vessels 2012 with the reaction mixtures are sealed via the automation subsystem 2006, such as via the above-described and further illustrated caps. The reaction vessels 2012 are selectively moved by the automation subsystem 2006 from the substrate 2014 that is proximal to the dispensing subsystem 2004 to the at least one reactor modules 2008. The automation subsystem 2006 moves specific vessels to different zones or reactor modules that are associated with different temperatures. For example, a first subset of the plurality of reaction vessels are moved to a first zone and/or first reactor module which drives the reactions within the first subset of reaction vessels by exposing the reaction mixtures to a first temperature (e.g., 50 degrees C.). A second subset of reaction vessels are moved to a second zone and/or a second reactor module, which exposes the second subset of reaction vessels to a second temperature (e.g., 75 degrees C.). A third subset are moved to a third zone and/or third reactor module and exposed to a third temperature. Embodiments are not limited to three zones, reactor modules and/or temperatures, and can include more or less than three, such as one, two, four, five, six, twenty, etc., zones, reactor modules, and/or temperatures.

Additionally, in various embodiments, respective reaction mixtures of the subset can be exposed to the respective temperatures for different periods of time. For example, the automation subsystem 2006 can selectively move (e.g., remove from the exposure to the temperature) reaction vessels from the at least one reactor module 2008 at different times based on the experimental design parameters 2001. Using the above-provided example, a first reaction vessel in the first subset is removed from the first zone and/or first reactor module after expiration of a first period of time (e.g., 2 minutes) and a second reaction vessel in the first subset is removed from the first zone and/or first reactor module after expiration of a second period of time (e.g., 2 minutes and twenty seconds). Although embodiments are not so limited, and the plurality of reaction vessels can be moved at the same time or at different periods of time to a location proximal to an analysis subsystem 2010 responsive to the plurality of reactions being driven to completion. For example, the automation subsystem 2006 can unseal the plurality of reaction vessels 2012 and selectively move reaction mixtures proximal to the analysis subsystem 2010. The analysis subsystem 2010 can then analyze the compositions, as compared to the target end product. In various embodiments, the reaction vessels 2012 can be unsealed by uncapping the reaction vessels 2012 (e.g., removing the cap that seal the reaction vessels 2012) or piercing a seal of the reaction vessels 2012. For example, the reaction vessels 2012 can include a seal that has a puncturable location that can be punctured to facilitate product retrieval and analysis.

The movement can be by the automation subsystem 2006. For example, for interfacing with a DART-MS, the reaction vessels 2012 can be placed on the substrate 2014, such as a 96-well plate. The automation subsystem 2006 caps the reaction vessels 2012, places the capped reaction vessels into the at least one reactor module 2008 as defined by the DOE information, and then removes them from the at least one reactor module 2008. The automation subsystem 2006 uncaps (or puts in a position to uncap) the reaction vessels 2012, and sequentially locates the uncapped reaction vessels in front of the DART inlet. For example, automation subsystem 2006 can place the uncapped reaction vessels on a conveyor that sequentially transports the reaction vessels in front of the DART inlet, as further illustrated herein.

In accordance with a number of embodiments, one or more of the synthetic reaction routes can include adding reagents at different times. In such embodiments, one or more reaction vessels are moved from the at least one reactor module 2008, unsealed or uncapped, moved back to the dispensing subsystem 2004 for dispensing one or more additional reagents, and optionally, recapped and moved back to one of the at least one reactor module 2008 for further driving the reaction. The automation subsystem 2006 selectively moves the reaction vessels from the at least one reactor module 2008 and/or the dispensing subsystem 2004 to a location in front of the DART-MS. In another embodiments, the reaction vessels are returned to the substrate 2014 or an additional substrate, e.g., well plate, and then the substrate is moved with an X-Y stage to position the vials in front of the DART-MS.

Although the above example describes use of a DART-MS, embodiments are not limited to DART-MS, to varied reaction conditions that include different temperatures and times, and/or to reaction vessels that can be individually moved. For example, the reaction mixtures can be dispensed in individual reaction vessels, capped, and reacted, as described above. The automation subsystem 2006 can replace the reaction vessels, as uncapped or otherwise unsealed (e.g., punctured), on or to the substrate 2014, and the reaction mixtures can be sampled directly with the LC-MS. In other embodiments, the reaction vessels are not vials that are individually selectable and/or movable. For example, the reagents can be dispensed directly into a substrate 2014 having wells, such as a microliter well plate. The substrate 2014 (e.g., plate) can be a traditional solid plate or a plate is compatible with a UV plate reader. In some embodiments, the apparatus 2000 is run in a screening mode in which all wells are exposed to the same temperature and the same time. In a screening mode, a variation of input reagents can be tested to identify which chemistries work. The dispensing subsystem 2004 dispenses the reagents into the well plate. For example, the plate is transported to the at least one reactor module 2008 for treatment (if needed), and then is placed on an LC-MS autosampler. In other embodiments, the reagents are dispensed into a transparent microtiter plate. The reaction mixtures are reacted with one set of reaction conditions and put on a plate reader for rapid UV/Vis assessment. In other specific embodiments, the (individual) reaction vessels 2012 include transparent vials where the reagents are dispensed, reacted individually (optimization), and then replaced on a transparent plate for UV/Vis analysis, such as described above.

Figure 21:
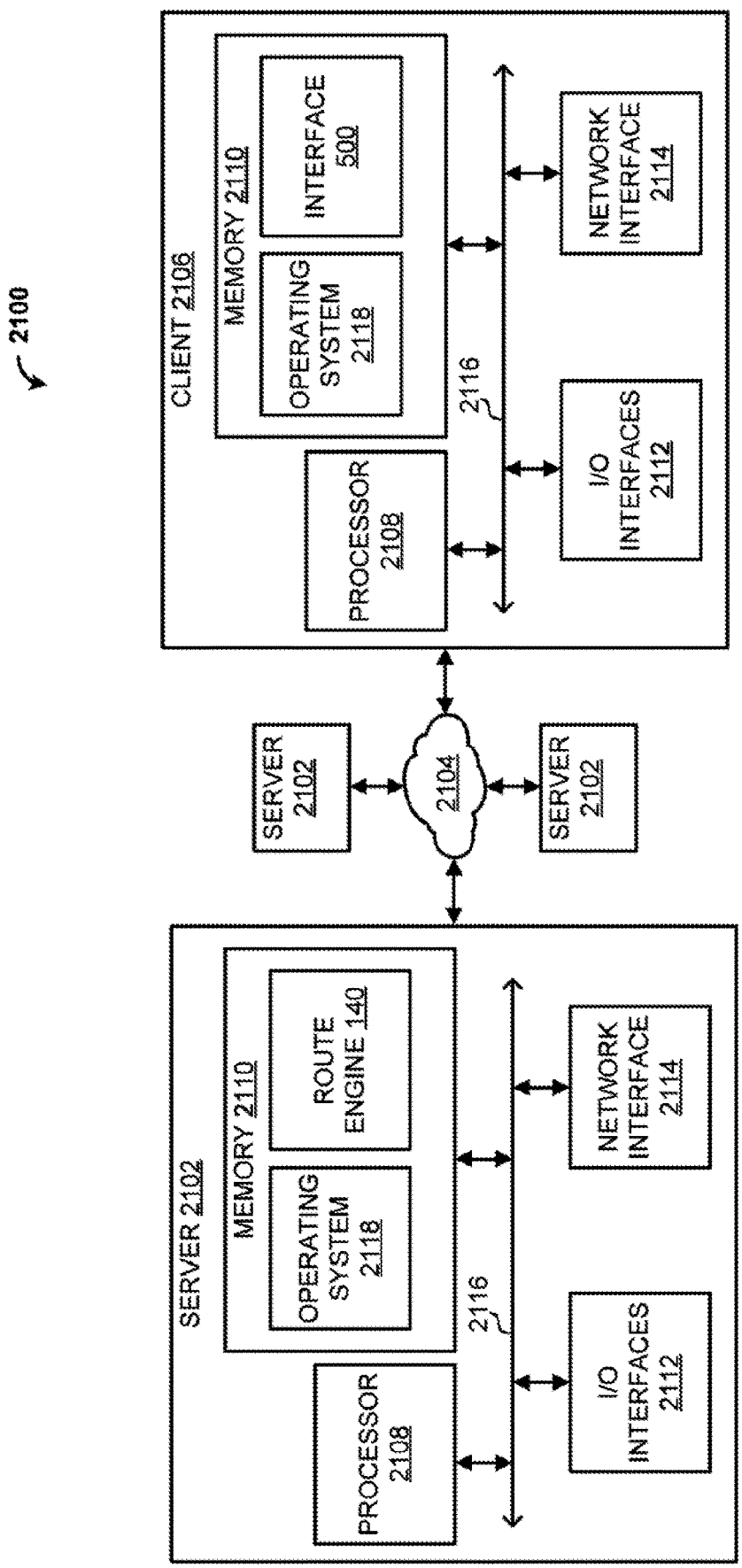
FIG. 21 shows a block diagram of an operating environment for implementing the described methods.

FIG. 21 is a block diagram depicting an environment 2100 comprising non-limiting examples of a server 2102 and a client 2106 connected through a network 2104. In an aspect, the analysis device 1700, the control module 1702, the computing device 1900, the remote computing device 1902, and/or the apparatus 2000 (and any subcomponents thereof) may comprise one or more of the server 2102 and/or the client 2106. In an aspect, some or all steps of any described method may be performed on a computing device as described herein. The server 2102 can comprise one or multiple computers configured to store one or more of the route engine 140, the reactions 110, the machine learning classifiers, the synthetic routes 150, and the like. The client 2106 can comprise one or multiple computers configured to operate the user interface 500 (e.g., via a web browser) such as, for example, a laptop computer or a desktop computer. Multiple clients 2106 can connect to the server(s) 2102 through a network 2104 such as, for example, the Internet. A user on a client 2106 may connect to the route engine 140 with the user interface 500.

The server 2102 and the client 2106 can be a digital computer that, in terms of hardware architecture, generally includes a processor 2108, memory system 2110, input/output (I/O) interfaces 2112, and network interfaces 2114. These components (2108, 2110, 2112, and 2114) are communicatively coupled via a local interface 2116. The local interface 2116 can be, for example but not limited to, one or more buses or other wired or wireless connections, as is known in the art. The local interface 2116 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 2108 can be a hardware device for executing software, particularly that stored in memory system 2110. The processor 2108 can be any custom made or commercially available processor, a central processing unit (CPU), an auxiliary processor among several processors associated with the server 2102 and the client 2106, a semiconductor-based microprocessor (in the form of a microchip or chip set), or generally any device for executing software instructions. When the server 2102 or the client 2106 is in operation, the processor 2108 can be configured to execute software stored within the memory system 2110, to communicate data to and from the memory system 2110, and to generally control operations of the server 2102 and the client 2106 pursuant to the software.

The I/O interfaces 2112 can be used to receive user input from and/or for providing system output to one or more devices or components. User input can be provided via, for example, a keyboard and/or a mouse. System output can be provided via a display device and a printer (not shown). I/O interfaces 2112 can include, for example, a serial port, a parallel port, a Small Computer System Interface (SCSI), an IR interface, an RF interface, and/or a universal serial bus (USB) interface.

The network interface 2114 can be used to transmit and receive from an external server 2102 or a client 2106 on a network 2104. The network interface 2114 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 2114 may include address, control, and/or data connections to enable appropriate communications on the network 2104.

The memory system 2110 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 2110 may incorporate electronic, magnetic, optical, and/or other types of storage media. Note that the memory system 2110 can have a distributed architecture, where various components are situated remote from one another, but can be accessed by the processor 2108.

The software in memory system 2110 may include one or more software programs, each of which comprises an ordered listing of executable instructions for implementing logical functions. In the example of FIG. 21, the software in the memory system 2110 of the server 2102 can comprise the route engine 140 and a suitable operating system (O/S) 2118. In the example of FIG. 21, the software in the memory system 2110 of the client 2106 can comprise the user interface 500 and a suitable operating system (O/S) 2118. The operating system 2118 essentially controls the execution of other computer programs, such as the operating system 2118, the user interface 500, and provides scheduling, input-output control, file and data management, memory management, and communication control and related services.

For purposes of illustration, application programs and other executable program components such as the operating system 2118 are illustrated herein as discrete blocks, although it is recognized that such programs and components can reside at various times in different storage components of the server 2102 and/or the client 2106. An implementation of the route engine 140 and/or the user interface 500 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

While specific configurations have been described, it is not intended that the scope be limited to the particular configurations set forth, as the configurations herein are intended in all respects to be possible configurations rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of configurations described in the specification.

It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

What is claimed is:

1. A method comprising:

determining, by a computing device, based on a first one or more sets of chemical reactions, a plurality of known chemical reactions;

determining, by the computing device, based on a target compound and generalized known chemical transformations, a plurality of computationally generated chemical reactions that is different from the plurality of known chemical reactions;

applying, by the computing device, a trained classifier to each of the plurality of computationally generated chemical reactions to classify one or more computationally generated chemical reactions from the plurality of computationally generated chemical reactions as successful computationally generated chemical reactions, the trained classifier comprising a machine learning model for execution by the computing device and trained using training data comprising one or more chemical reactions categorized as successful and one or more chemical reactions categorized as unsuccessful;

generating, by the computing device, based on the one or more successful computationally generated chemical reactions and the plurality of known chemical reactions, a plurality of chemical reactions, wherein each chemical transition of the plurality of chemical reactions represents a transformation of a first compound to a second compound;

determining, by the computing device, based on the target compound, a plurality of chemical synthesis routes, wherein each chemical synthesis route of the plurality of chemical synthesis routes comprises one or more chemical reactions of the plurality of chemical reactions and each chemical synthesis route of the plurality of chemical synthesis routes produces the target compound;

identifying, by the computing device, a chemical synthesis route of the plurality of chemical synthesis routes having a corresponding cost less than a threshold; and performing chemical synthesis of the identified chemical synthesis route to synthesize the target compound.

2. The method of claim 1, further comprising training, by the computing device, a classifier on a training data set, wherein the training data set comprises one or more of, a chemical reaction database, estimated yields, or predicted yields for the one or more sets of chemical reactions.

3. The method of claim 2, wherein training the classifier on the training data set comprises:

receiving a dataset comprising the plurality of known chemical reactions, wherein each of the plurality of known chemical reactions comprises at least one reactant, wherein each reactant of the at least one reactant is comprised of one or more atoms;

for each reactant of the at least one reactant, classifying the one or more atoms into one or more categories based on a neighborhood atom, a bond order, a number of hydrogen atoms present, or a combination of one or more of the neighborhood atom, the bond order, or the number of hydrogen atoms present;

for each reactant of the at least one reactant, determining a vector based on a histogram of the one or more categories;

determining the training data set, wherein the training data set is comprised of a) vectors of reactions associated with a specific transformation and b) vectors of reactions associated with the specific transformation but yield a product from a different reaction type;

exposing the classifier to a portion of the training data set to train the classifier; and exposing the trained classifier to another portion of the training data set to test the trained classifier.

4. The method of claim 3, wherein exposing the trained classifier to another portion of the training data set to test the trained classifier comprises assessing performance of the trained classifier based on one or more metrics.

5. The method of claim 4, wherein the one or more metrics comprise one or more of accuracy, positive precision, negative precision, positive recall, or negative recall.

6. The method of claim 1, further comprising generating, by the computing device, a tree data structure, wherein the target compound is a root node of the tree data structure.

7. The method of claim 6, further comprising adding, by the computing device, to the tree data structure, a plurality of branches, wherein each branch of the plurality of branches comprises a chemical synthesis route of the plurality of chemical synthesis routes.

8. The method of claim 1, wherein determining the plurality of chemical synthesis routes associated with the target compound is based on one or more parameters.

9. The method of claim 8, wherein the one or more parameters comprise one or more of available feedstock, available chemical substances, or available equipment.

10. The method of claim 1, wherein determining the plurality of chemical synthesis routes is based on one or more parameters.

11. The method of claim 10, wherein the one or more parameters comprise one or more of available feedstock, available chemical substances, available equipment, yield, financial cost, time, reaction conditions, or likelihood of reaction success.

12. The method of claim 1, wherein determining the plurality of chemical synthesis routes comprises:

determining all compounds that can reach the target compound in at most a predefined number of steps, and wherein identifying the chemical synthesis route of the plurality of chemical synthesis routes having a corresponding cost less than a threshold comprises determining, from among the plurality of chemical synthesis routes including routes that exclude work-up or solvent exchange steps, a minimal cost chemical synthesis route to the target compound.

13. The method of claim 12, wherein determining the minimal cost chemical synthesis route comprises evaluating a cost function.

14. The method of claim 13, wherein the cost function comprises:

$$\text{Cost}(C_R) = I\text{Cost}(R) + \left( \sum_{C \in Reactants(R)} \text{Cost}(C_{R_i}) + \sum_{f \in Feedstocks(R)} f_{cost} \right) / R_{yield}$$

where $C_R$ is a compound C produced by reaction R $I\text{Cost}(R)$ is a fixed cost to implement reaction R $C_{R_i}$ is a reactant of R produced by some reaction $R_i$ $f_{cost}$ is a fixed cost for feedstock f $R_{yield}$ is the yield of reaction R, $0 < R_{yield} \leq 1$.

15. The method of claim 1, further comprising: outputting an indication of the identified chemical synthesis route.

16. The method of claim 1, wherein the plurality of known chemical reactions and the plurality of computationally generated chemical reactions are disjointed sets.

17. The method of claim 1, wherein a set of the first one or more sets of chemical reactions is a reaction database.

18. The method of claim 1, wherein the trained classifier is based on vectors of reactions associated with a specific transformation.

19. A method comprising:
  receiving feedstock; and
  synthesizing a target compound from the feedstock routed by a process comprising:
   determining, based on one or more sets of chemical reactions, a plurality of known chemical reactions;
   determining, based on a target compound and generalized known chemical transformations, a plurality of computationally generated chemical reactions that is different from the plurality of known chemical reactions;
   applying a trained classifier to each of the plurality of computationally generated chemical reactions to classify one or more computationally generated chemical reactions from the plurality of computationally generated chemical reactions as successful computationally generated chemical reactions, the trained classifier comprising a machine learning model for execution by the computing device and trained using training data comprising one or more chemical reactions categorized as successful and one or more chemical reactions categorized as unsuccessful;
   generating, based on the one or more successful computationally generated chemical reactions and the plurality of known chemical reactions, a plurality of chemical reactions, wherein each chemical transition of the plurality of chemical reactions represents a transformation of a first compound to a second compound;
   determining, based on the target compound, a plurality of chemical synthesis routes, wherein each chemical synthesis route of the plurality of chemical synthesis routes comprises one or more chemical reactions of the plurality of chemical reactions and each chemical synthesis route of the plurality of chemical synthesis routes produces the target compound;
   identifying a chemical synthesis route of the plurality of chemical synthesis routes having a corresponding cost less than a threshold; and
   performing chemical synthesis of the identified chemical synthesis route to synthesize the target compound from the feedstock.

* * * * *